(12) United States Patent
Hashimoto et al.

(10) Patent No.: US 7,964,292 B2
(45) Date of Patent: Jun. 21, 2011

(54) METAL COMPLEX, LIGHT-EMITTING DEVICE, AND DISPLAY APPARATUS

(75) Inventors: Masashi Hashimoto, Tokyo (JP); Takao Takiguchi, Tokyo (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 1097 days.

(21) Appl. No.: 11/689,728

(22) Filed: Mar. 22, 2007

(65) Prior Publication Data

US 2007/0228940 A1 Oct. 4, 2007

(30) Foreign Application Priority Data

Mar. 31, 2006 (JP) ................................. 2006-099894

(51) Int. Cl.
*H01L 51/54* (2006.01)
*C09K 11/06* (2006.01)
(52) U.S. Cl. . 428/690; 428/917; 313/504; 257/E51.044; 546/4; 546/10; 544/64
(58) Field of Classification Search ........................ None
See application file for complete search history.

(56) References Cited

U.S. PATENT DOCUMENTS

| 6,824,894 | B2 | 11/2004 | Takiguchi et al. | 428/690 |
|---|---|---|---|---|
| 6,838,818 | B2 | 1/2005 | Furugori et al. | 313/504 |
| 7,022,422 | B2 | 4/2006 | Hamada et al. | 428/690 |
| 7,108,924 | B2 | 9/2006 | Kamatani et al. | 428/690 |
| 7,767,777 | B2 * | 8/2010 | Buesing et al. | 528/9 |
| 2005/0123798 | A1 | 6/2005 | Deaton et al. | 428/690 |
| 2005/0221115 | A1 | 10/2005 | Tsuboyama et al. | 428/690 |
| 2005/0276994 | A1 | 12/2005 | Iwawaki et al. | 428/690 |
| 2006/0066225 | A1 | 3/2006 | Kishino et al. | 313/504 |
| 2006/0197077 | A1 * | 9/2006 | Okuda et al. | 257/40 |
| 2006/0280968 | A1 | 12/2006 | Kamatani et al. | 428/690 |
| 2007/0207344 | A1 | 9/2007 | Kamatani et al. | 428/690 |
| 2007/0231600 | A1 | 10/2007 | Kamatani et al. | 428/690 |
| 2007/0232803 | A1 | 10/2007 | Kamatani et al. | 546/2 |

FOREIGN PATENT DOCUMENTS

| JP | 2003-253256 | | 9/2003 |
|---|---|---|---|
| JP | 2004-87390 | A * | 3/2004 |
| WO | WO 01/72927 | | 10/2001 |
| WO | WO 2004/056839 | | 7/2004 |
| WO | WO 2005/007767 | | 1/2005 |

OTHER PUBLICATIONS

Machine translation for JP 2004-87390 (Mar. 2004).*
Perez et al., "Synthesis and Structure of the First Ruthenated Benzodiazepines", Organometallics, vol. 21, No. 24, pp. 5437-5438 (2002).*
Burroughes et al., "Light-emitting Diodes Based on Conjugated Polymers," *Nature*, vol. 347, 539-541 (1990).
Baldo et al., "Very High-efficiency Green Organic Light-emitting Devices Based on Electrophosphorescence," *Appl. Phys. Lett.*, vol. 75, No. 1, 4-6 (1999).
Van Gorkom et al., "Micromagnetics and Magnetoresistance of a Permalloy Point Contact," *Appl. Phys. Lett.*, vol. 74, No. 3, 422-424 (1999).
Vincett et al., "Electrical Conduction and Low Voltage Blue Electroluminescence in Vacuum-deposited Organic Films," *Thin Solid Films*, vol. 94, 171-183 (1982).
Nagubandi et al., "The Mechanism of the Bischler-Napieralski Reaction," *J. Heterocyclic Chem.*, vol. 17, 1457-1463 (1980).
Al-Arab, M. M., "A Simple Synthesis of Novel 2-Pyridones from Chalcones," *J. Heterocyclic Chem.*, vol. 27, 523-525, (1990).
Brodrick et al., "Amidines. Part XVI. A New Synthesis of 1-Alkyl- and 1-Aryl-3: 4-Dihydroisoquinolines," *J. Chem. Soc.*, Part II, (1951), 1343-1345 .
Gilman et al., "Atropisomers of 1,4-Benzodiazepines. Synthesis and Resolution of a Diazepam-Related 1,4-Benzodiazepine," *J. Am. Chem. Soc.*, vol. 112, 3969-3978 (1990).
Lantos et al., "Synthesis of 9-Phenyl-5 *H*-2-Benzazepines by Ring Expansion of 1-Phenyl-2,3-dihydroisoquinolines," *J. Org. Chem.*, vol. 51, 4147-4150 (1986).
Bradsher et al., "α-Acyl-o-tolunitriles as Intermediates in the Preparation of 3-Substituted Isoquinolines and 1-Amino-2-benzopyrylium Derivatives," *J. Org. Chem.*, vol. 43, No. 20, 3817-3820 (1978).
Gates, Marshall, "New Synthesis of Diazepam," *J. Org. Chem.*, vol. 45, 1675-1681 (1980).
Salathiel et al., "Synthesis of Some New Alpha-Substituted Tetrahydropyridines and Piperidines," vol. 59, 984-986 (1937), JACS.
Sezen et al., "Oxidative C-Arylation of Free (NH)-Heterocycles via Direct ($sp^3$) C-H Bond Functionalization," *J. Am. Chem. Soc.*, vol. 126, 13244-13246 (2004).
Zezza et al., "Reaction of Organolithium Reagents with Lactim Ethers: Preparation of Cyclic 2-Alkyl Imines or 2,2-Dialkyl Amines," *J. Org. Chem.* vol. 49, 4397-4399 (1984).
Boivin et al., "A Flexible, Convergent Approach to Piperidines, Pyridines, Azepines, and Related Derivatives," *Tetrahedron Letters*, vol. 40, 3701-3704 (1999).
Pal et al., "A General Stereocontrolled Synthesis of *cis*-2,3 Disubstituted Pyrrolidines and Piperidines," *Tetrahedron Letters*, vol. 34, No. 39, 6205-6208 (1993).

(Continued)

*Primary Examiner* — Marie R. Yamnitzky
(74) *Attorney, Agent, or Firm* — Fitzpatrick, Cella, Harper & Scinto

(57) ABSTRACT

A metal complex is provided which is used for an organic EL device and an organic light-emitting device which outputs light with high luminance and high efficiency. The metal complex has a structure in which a nitrogen atom in a 6- to 8-membered non-aromatic cyclic group is bonded to a metal atom. The organic light-emitting device includes a pair of electrodes which are an anode and a cathode, and an organic compound layer interposed between the electrodes. The organic compound layer contains the metal complex represented by the following structural formula.

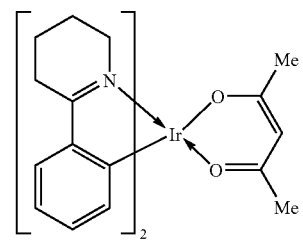

4 Claims, 3 Drawing Sheets

OTHER PUBLICATIONS

Cooke et al., "Synthesis of 2-Methoxy- and 2-Phenoxypenems," *Tetrahedron Letters,* vol. 24, No. 32, 3373-3376 (1983).

Banks et al., "N-Halogeno Compounds, Part 12 [1], Site-specific Fluorination of Carbanions with Porfluoro-N-Fluoropiperidine (2)," *J. Fluorine Chem.,* vol. 52, 389-401 (1991).

Chen et al., "Recent Developments in Molecular Organic Electroluminescent Materials," *Macromol. Symp.* vol. 125, 1-48 (1997).

* cited by examiner

METAL COMPLEX, LIGHT-EMITTING DEVICE, AND DISPLAY APPARATUS

BACKGROUND OF THE INVENTION

1. Field of the Invention

The present invention relates to a novel metal complex, and a light-emitting device and a display apparatus using the metal complex.

2. Description of the Related Art

In an old example of an organic light-emitting device, a voltage has been applied to an anthracene evaporated film to emit light (see, Thin Solid Films, 94 (1982), 171). In recent years, applied research has been vigorously conducted on a transformation of an organic light-emitting device into a light-emitting device having high-speed response and high efficiency, including developments of materials for the device. This is because the organic light-emitting device has such advantages that its area can be increased more easily than an inorganic light-emitting device, desired colors can be developed through the developments of various new materials, and it can be operated at a low voltage.

For example, as described in detail in Macromol. Symp. 125, 1 to 48 (1997), an organic electroluminescence device (hereinafter referred to also as an "organic EL device") is generally composed of a transparent substrate, a pair of upper and lower electrode layers formed on the transparent substrate and an organic material layer interposed therebetween including a light-emitting layer.

Recently, investigation has been made into a device utilizing not only conventional light emission utilizing fluorescence ascribable to a transition from an excited singlet state to a ground state but also phosphorescence via a triplet exciton as typified by technologies described in "Improved energy transfer in electrophosphoresent device", D. F. O'Brien et al., Applied Physics Letters, Vol 74, No. 3, p 422 (1999) and "Very high-efficiency green organic light-emitting devices based on electrophosphorescence", M. A. Baldo et al., Applied Physics Letters, Vol 75, No. 1, p 4 (1999). In each of those documents, an organic layer having a four-layer structure has been mainly used. The organic layer includes, from an anode side, a hole-transporting layer, a light-emitting layer, an exciton diffusion preventing layer, and an electron-transporting layer. Materials used are a carrier-transporting material and a phosphorescent material Ir(ppy)$_3$ shown below.

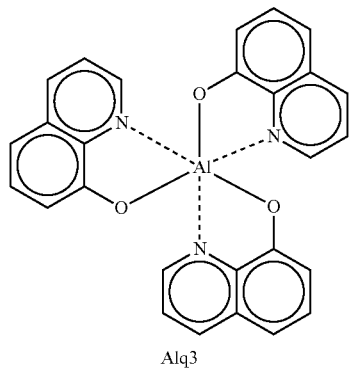

Alq3

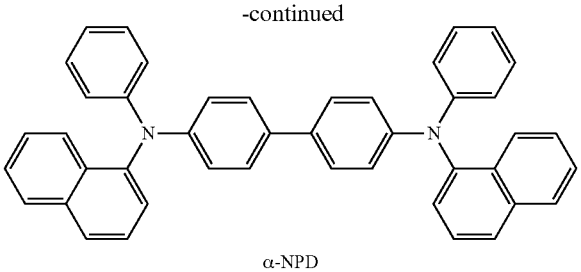

α-NPD

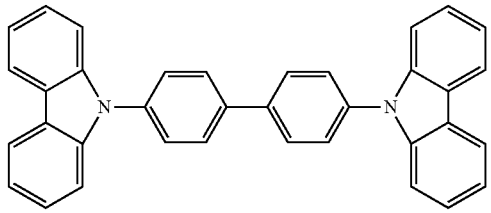

CBP

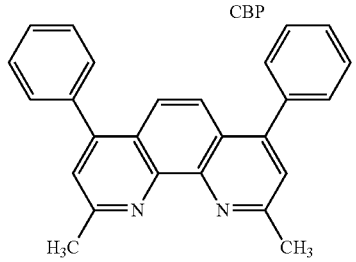

BCP

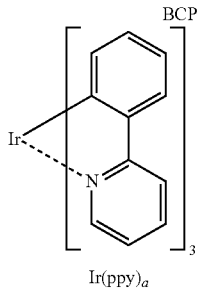

Ir(ppy)$_3$

A variety of light ranging from ultraviolet light to infrared light can be emitted by changing the types of fluorescent organic compounds. In recent years, active research has been conducted on various compounds.

In addition to an organic light-emitting device using any one of the low-molecular-weight materials as described above, an organic light-emitting device using a conjugated polymer has been reported by a group at the University of Cambridge (see, Nature, 347, 539 (1990)). In this report, there has been observed light emission from a single layer by forming polyphenylenevinylene (PPV) into a film by means of a coating system.

As described above, an organic light-emitting device has recently showed significant progress. The organic light-emitting device can be transformed into a high-speed response, thin, and lightweight light-emitting device which can be driven at a low applied voltage and has high luminance and a variety of emission wavelengths, thus suggesting possibilities of a wide variety of applications. However, under the present conditions, a light output higher in luminance and higher conversion efficiency are being sought. In addition, there still remain a large number of problems in terms of durability such as changes over time during long-term use and deterioration due to atmospheric gases containing oxygen or moisture. Further, luminescence of blue, green, and red which have good color purity are necessary when the organic light-emitting device is applied to a full-color display, but this issue as well has not been satisfactorily solved.

In addition, a large number of condensed polycyclic aromatic compounds have been investigated for their potential as a fluorescent organic compound to be used in an electron-transporting layer and the like. However, no compounds with sufficient luminance and durability have been produced.

WO 01/072927, Japanese Patent No. 3,605,083, WO 2004-056839, WO 2005-007767, and US 2005-123798 describe applications of metal complex compounds related to the present invention to organic EL devices.

SUMMARY OF THE INVENTION

An object of the present invention is to provide a metal complex to be used for an organic EL device, having a structure in which a nitrogen atom in a 6- to 8-membered non-aromatic cyclic group is bonded to a metal atom, an organic light-emitting device which is produced by using the metal complex and outputs light with high efficiency and high luminance, and a display apparatus using the light-emitting device.

None of the patent documents and non-patent documents as mentioned above discloses or suggests the metal complex compound of the present invention, i.e., a metal complex in which a nitrogen atom which coordinates with a metal is included in a 6- to 8-membered non-aromatic cyclic group.

That is, the present invention provides a metal complex having a partial structure represented by the following general formula (1):

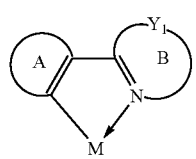

General Formula (1)

wherein a ring structure A represents an aromatic cyclic group having a carbon atom which is bonded to M, and may have at least one substituent selected from the group consisting of a halogen atom; a nitro group; an aryl group; a heteroaryl group; a dialkylamino group; a trialkylsilyl group having 1 to 8 carbon atoms; a linear or branched alkoxyl group having 1 to 20 carbon atoms in which one or unadjacent two or more methylene groups in the alkoxyl group may be replaced by at least one group selected from the group consisting of —O—, —S—, —CO—, —CO—O—, —O—CO—, —CH=CH— and —C≡C—, and one or two or more hydrogen atoms in the alkoxyl group may be replaced by a fluorine atom; and a linear or branched alkyl group having 1 to 20 carbon atoms in which one or unadjacent two or more methylene groups in the alkyl group may be replaced by at least one group selected from the group consisting of —O—, —S—, —CO—, —CO—O—, —O—CO—, —CH=CH— and —C≡C—, and one or two or more hydrogen atoms in the alkyl group may be replaced by a fluorine atom; provided that the substituents may be combined together to form a ring structure; a ring structure B represents a 6- to 8-membered non-aromatic cyclic group having a nitrogen atom which is bonded to M, and may have at least one substituent selected from the group consisting of a halogen atom; a nitro group; an aryl group; a heteroaryl group; a dialkylamino group; a trialkylsilyl group having 1 to 8 carbon atoms; a linear or branched alkoxyl group having 1 to 20 carbon atoms in which one or unadjacent two or more methylene groups in the alkoxyl group may be replaced by at least one group selected from the group consisting of —O—, —S—, —CO—, —CO—O—, —O—CO—, —CH=CH— or —C≡C—, and one or two or more hydrogen atoms in the alkoxyl group may be replaced by a fluorine atom; and a linear or branched alkyl group having 1 to 20 carbon atoms in which one or unadjacent two or more methylene groups may be substituted by —O—, —S—, —CO—, —CO—O—, —O—CO—, —CH=CH— or —C≡C—, and one or two or more hydrogen atoms in the alkyl group may be substituted by a fluorine atom; provided that the substituents may be combined together to form a ring structure; $Y_1$ represents an alkylene group having 4 to 6 carbon atoms in which one or two methylene groups in the alkylene group may be replaced by at least one group selected from the group consisting of —O—, —CO—, —CO—O—, —O—CO—, —S—, —$CR_1$=$CR_2$— and —$NR_3$— (where $R_1$ to $R_3$ are each independently a hydrogen atom, an aryl group, a heteroaryl group or a linear or branched alkyl group having 1 to 10 carbon atoms in which one or two or more hydrogen atoms in the alkyl group may be replaced by a fluorine atom, provided that the substituents may be combined together to form a ring structure), and one or two or more hydrogen atoms in the alkylene group may be replaced by at least one of a fluorine atom and a linear or branched alkyl group having 1 to 10 carbon atoms in which one or two or more hydrogen atoms in the alkyl group may be replaced by a fluorine atom, provided that the substituents may combined together to form a ring structure; and M is a metal atom selected from the group consisting of Ir, Pt, Rh, and Ru.

Further, according to the present invention, in the metal complex represented by the general formula (1), the partial structure is represented by any one of the general formulae (2) to (4):

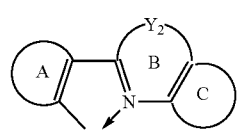

General Formula (2)

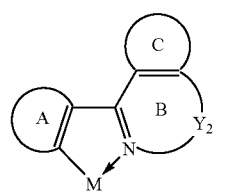

General Formula (3)

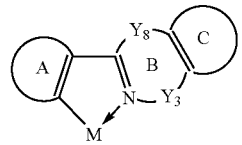

General Formula (4)

wherein a ring structure A represents a cyclic group having a carbon atom which is bonded to M, and may have at least one substituent selected from the group consisting of: a halogen atom; a nitro group; an aryl group; a heteroaryl group; a dialkylamino group; a trialkylsilyl group having 1 to 8 carbon atoms; a linear or branched alkoxyl group having 1 to 20 carbon atoms in which one or unadjacent two or more methylene groups in the alkoxyl group may be replaced by at least one group selected from the group consisting of —O—, —S—, —CO—, —CO—O—, —O—CO—, —CH=CH— and —C≡C—, and one or two or more hydrogen atoms in the alkoxyl group may be replaced by a fluorine atom; and a linear or branched alkyl group having 1 to 20 carbon atoms in which one or unadjacent two or more methylene groups in the alkyl group may be replaced by at least one group selected from the group consisting of —O—, —S—, —CO—, —CO—O—, —O—CO—, —CH=CH— and —C≡C—, and one or two or more hydrogen atoms in the alkyl group may be replaced by a fluorine atom, provided that the substituents may be combined together to form a ring structure; a ring structure B represents a 6- to 8-membered non-aromatic cyclic group having a nitrogen atom which is bonded to M, and may have at least one substituent selected from the group consisting of: a halogen atom; a nitro group; an aryl group; a heteroaryl group; a dialkylamino group; a trialkylsilyl group having 1 to 8 carbon atoms; a linear or branched alkoxyl group having 1 to 20 carbon atoms in which one or unadjacent two or more methylene groups in the alkoxyl group may be replaced by at least one group selected from the group consisting of —O—, —S—, —CO—, —CO—O—, —O—CO—, —CH=CH— and —C≡C—, and one or two or more hydrogen atoms in the alkoxyl group may be substituted by a fluorine atom; and a linear or branched alkyl group having 1 to 20 carbon atoms in which one or unadjacent tow or more methylene groups in the alkyl group may be replaced by at least one group selected from the group consisting one of —O—, —S—, —CO—, —CO—O—, —O—CO—, —CH=CH— and —C≡C—, and one or two or more hydrogen atoms in the alkyl group may be substituted by a fluorine atom; provided that the substituents may be combined together to form a ring structure; $Y_2$ represents an alkylene group having 2 to 4 carbon atoms in which one or two or more methylene groups in the alkylene group may be replaced by at least one group selected from the group consisting of —O—, —CO—, —CO—O—, —O—CO—, —S—, —$CR_1$=$CR_2$— and —$NR_3$— (where $R_1$ to $R_3$ are each independently a hydrogen atom, an aryl group, a heteroaryl group or a linear or branched alkyl group having 1 to 10 carbon atoms in which one or two or more hydrogen atoms in the alkyl group may be replaced by a fluorine atom, provided that the substituents may be combined together to form a ring structure), and one or two or more hydrogen atoms in the alkylene group may be replaced by at least one of a fluorine atom and a linear or branched alkyl group having 1 to 10 carbon atoms in which one or two or more hydrogen atom in the alkyl group may be substituted by a fluorine atom, and a fluorine atom, provided that the substituents may be combined together to form a ring structure; $Y_3$ represents an alkylene group having 1 to 3 carbon atoms (provided that two $Y_3$'s have 2 to 4 carbon atoms in total) in which one or two methylene groups in the alkylene group may be substituted by at least one group selected from the group consisting of —O—, —CO—, —CO—O—, —O—CO—, —S—, —$CR_1$=$CR_2$— and —$NR_3$— (where $R_1$ to $R_3$ are each independently an aryl group, a heteroaryl group, a hydrogen atom or a linear or branched alkyl group having 1 to 10 carbon atoms in which one or two or more hydrogen atoms in the alkyl group may be substituted by a fluorine atom, provided that the substituents may be combined together to form a ring structure), and one or two or more hydrogen atoms in the alkylene group may be substituted by at least one of a fluorine atom and a linear or branched alkyl group having 1 to 10 carbon atoms in which one or two or more hydrogen atoms in the alkyl group may be replaced by a fluorine atom, provided that the substituents may be combined together to form a ring structure; a ring structure C represents an aromatic cyclic group condensed with the ring structure B, and may have at least one substituent selected from the group consisting of a halogen atom; a nitro group; an aryl group; a heteroaryl group; a dialkylamino group; a trialkylsilyl group having 1 to 8 carbon atoms; a linear or branched alkoxyl group having 1 to 20 carbon atoms in which one or unadjacent two or more methylene groups in the alkoxyl group may be replaced by at least one group selected from the group consisting of —O—, —S—, —CO—, —CO—O—, —O—CO—, —CH=CH— and —C≡C—, and one or two or more hydrogen atoms in the alkoxyl group may be replaced by a fluorine atom; and a linear or branched alkyl group having 1 to 20 carbon atoms in which one or unadjacent two or more methylene groups in the alkyl group may be replaced by at least on group selected from the group consisting of —O—, —S—, —CO—, —CO—O—, —O—CO—, —CH=CH— and —C≡C—, and one or two or more hydrogen atoms in the alkyl group may be replaced by a fluorine atom, provided that the substituents may be combined together to form a ring structure; and M is a metal atom selected from the group consisting of Ir, Pt, Rh, and Ru.

Further, according to the present invention, in the metal complex, the partial structure is represented by the general formula (5):

$$ML1_mL2_n \qquad \text{General Formula (5)}$$

where L1 and L2 represent bidentate ligands different from each other; m represents 1, 2 or 3, and n represents 0, 1 or 2, provided that m+n is 2 or 3; a partial structure ML1 is represented by any one of the general formulae (2), (3), and (4) described in claim 2, and a partial structure ML2 is represented by any one of the general formulae (6), (7) and (8):

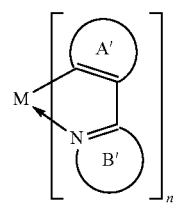

General Formula (6)

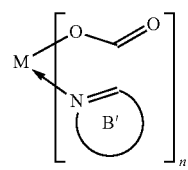

General Formula (7)

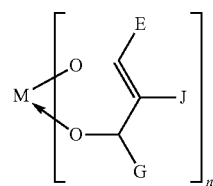

General Formula (8)

where N represents a nitrogen atom; A' represents a cyclic group which may be substituted and is bonded to a metal atom M via a carbon atom, and B' represents a cyclic group which may be substituted and is bonded to the metal atom M via a nitrogen atom, each of A' and B' being bonded by covalent bond; E and G are each independently a linear or branched alkyl group having 1 to 20 carbon atoms (in which one or unadjacent methylene groups in the alkyl group may be replaced by at least one group selected from the group consisting of —O—, —S—, —CO—, —CO—O—, —O—CO—, —CH=CH— and —C≡C—, and one or two or more hydrogen atoms in the alkyl group may be replaced by a fluorine atom); or an aromatic cyclic group which may have at least one substituent selected from the group consisting of a halogen atom, a cyano group, a nitro group, a trialkylsilyl group whose alkyl groups are each independently a linear or branched alkyl group having 1 to 8 carbon atoms, a linear or branched alkoxyl group having 1 to 20 carbon atoms (in which one or unadjacent two or more methylene groups in the alkoxyl group may be replaced by at least one group selected from the group consisting of —O—, —S—, —CO—, —CO—O—, —O—CO—, —CH=CH— and —C≡C—, and one or two or more hydrogen atoms in the alkoxyl group may be replaced by a fluorine atom), and a linear or branched alkyl group having 1 to 20 carbon atoms (in which one or unadjacent two or more methylene groups in the alkyl group may be replaced by at least one group selected from the group consisting of —O—, —S—, —CO—, —CO—O—, —O—CO—, —CH=CH— and —C≡C—, and one or two or more hydrogen atoms in the alkyl group may be replaced by a fluorine atom); J represents a hydrogen atom; a halogen atom; a linear or branched alkyl group having 1 to 20 carbon atoms in which one or two or more hydrogen atoms in the alkyl group may be replaced by a fluorine atom; or an aromatic cyclic group which may have at least one substituent selected from the group consisting of a halogen atom, a cyano group, a nitro group, a trialkylsilyl group whose alkyl groups are each independently a linear or branched alkyl group having 1 to 8 carbon atoms, a linear or branched alkoxyl group having 1 to 20 carbon atoms (in which one or unadjacent two or more methylene groups in the alkoxyl group may be replaced by at least one group selected from the group consisting of —O—, —S—, —CO—, —CO—O—, —O—CO—, —CH=CH— and —C≡C—, and one or two or more hydrogen atoms in the alkoxyl group may be replaced by a fluorine atom), and a linear or branched alkyl group having 1 to 20 carbon atoms (in which one or unadjacent two or more methylene groups in the alkyl group may be substituted by at least one group selected from the group consisting of —O—, —S—, —CO—, —CO—O—, —O—CO—, —CH=CH— and —C≡C—, and one or two or more hydrogen atoms in the alkyl group may be replaced by a fluorine atom); and M is a metal atom selected from the group consisting of Ir, Pt, Rh, and Ru.

Further, according to the present invention, $Y_1$, $Y_2$, and $Y_3$ forming the metal complex are each independently an alkylene group which may be substituted, in which one or two methylene groups in the alkylene group may be replaced by —$CR_1$=$CR_2$— (where $R_1$ and $R_2$ are each independently an aryl group, a heteroaryl group, a hydrogen atom or a linear or branched alkyl group having 1 to 10 carbon atoms (in which one or two or more hydrogen atoms in the alkyl group may be substituted by a fluorine atom, provided that the substituents may be combined together to form a ring structure), and one or two or more hydrogen atoms in the alkylene group may be replaced by at least one of a fluorine atom and a linear or branched alkyl group having 1 to 10 carbon atoms in which one or two or more hydrogen atoms in the alkyl group may be replaced by a fluorine atom), provided that the substituents may be combined together to form a ring structure.

Further, according to the present invention, there is provided an organic light-emitting device including: a pair of electrodes; and an organic compound layer which is interposed between the electrodes, in which the organic compound layer includes the metal complex represented by the general formula (1).

Further, according to the present invention, in the organic light-emitting device, the organic compound layer is a light-emitting layer.

Further, according to the present invention, there is provided a display apparatus including the above-mentioned organic light-emitting device.

According to the present invention, there are provided a metal complex to be used for an organic EL device, having a structure in which a nitrogen atom in a 6- to 8-membered non-aromatic cyclic group is bonded to a metal atom and a light-emitting device using the metal complex which outputs light with high efficiency and high luminance.

The light-emitting device of the present invention serves as an excellent display device. By using the metal complex of the present invention, phosphorescent luminescence of red color can be obtained, so the light-emitting device using the metal complex of the present invention can provide a full-color display apparatus.

Further features of the present invention will become apparent from the following description of exemplary embodiments with reference to the attached drawings.

DESCRIPTION OF THE EMBODIMENTS

Figure 1:
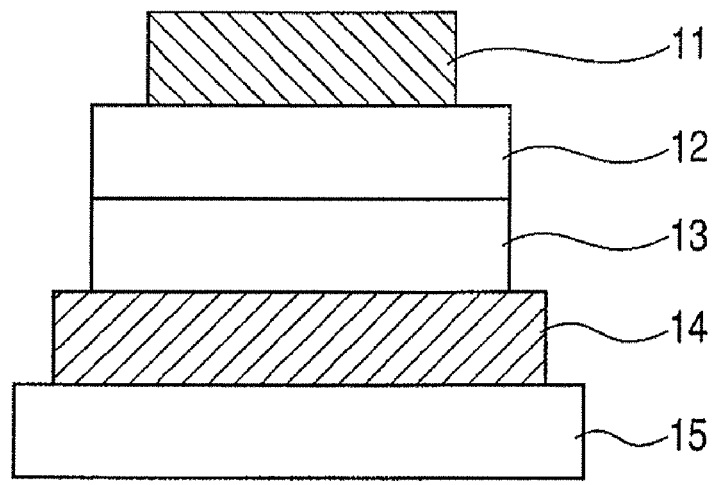
FIG. 1 shows an example of an organic EL device of the present invention.

Hereinafter, the present invention will be described in detail.

First, the metal complex that is the organic compound of the present invention is described.

The metal complex of the present invention has a partial structure represented by the general formula (1) including an aromatic cyclic group (A) and a 6- to 8-membered non-aromatic cyclic group (B) having a nitrogen atom.

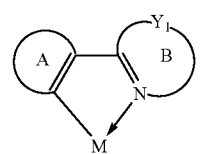

General Formula (1)

A ring structure A represents an aromatic cyclic group having a carbon atom which is bonded to M, and may have at least one substituent selected from the group consisting of a halogen atom; a nitro group; an aryl group; a heteroaryl group; a dialkylamino group; a trialkylsilyl group having 1 to 8 carbon atoms; a linear or branched alkoxyl group having 1 to 20 carbon atoms in which one or unadjacent two or more methylene groups in the alkoxyl group may be substituted by at least one group selected from the group consisting of —O—, —S—, —CO—, —CO—O—, —O—CO—, —CH═CH— and —C≡C—, and one or two or more hydrogen atoms in the alkoxyl group may be replaced by a fluorine atom; and a linear or branched alkyl group having 1 to 20 carbon atoms in which one or unadjacent two or more methylene groups in the alkyl group may be replaced by at least one group selected from the group consisting of —O—, —S—, —CO—, —CO—O—, —O—CO—, —CH═CH— and —C≡C—, and one or two or more hydrogen atoms in the alkyl group may be substituted by a fluorine atom; provided that the substituents may be combined together to form a ring structure.

The ring structure A is an aromatic cyclic group having a carbon atom which is bonded to M. Examples of the cyclic group include a phenyl group, a naphthyl group, an anthranyl group, a fluorenyl group, a pyrenyl group, a phenanthrenyl group, a chrysenyl group, a fluoranthenyl group, a triphenylenyl group, a perylenyl group, a pyridyl group, a pyrazinyl group, a pyrimidyl group, a pyridazinyl group, a quinolinyl group, an isoquinolinyl group, a phenanthridinyl group, an acridinyl group, a naphthyridinyl group, a quinoxalinyl group, a quinazolinyl group, a cinnolinyl group, a phthalazinyl group, a phenanthrolyl group, a phenazinyl group, a thiazolyl group, a thienyl group, a furanyl group, a pyrrolyl group, an imidazolyl group, a benzothienyl group, a benzofuranyl group, an indolyl group, a dibenzothienyl group, a dibenzofuranyl group, and a carbazolyl group. Preferable examples of the cyclic group include a phenyl group, a naphthyl group, an anthranyl group, a fluorenyl group, a phenanthrenyl group, a chrysenyl group, a triphenylenyl group, a pyridyl group, a pyrazinyl group, a pyrimidyl group, a pyridazinyl group, a quinolinyl group, an isoquinolinyl group, a naphthyridinyl group, a quinoxalinyl group, a thienyl group, a furanyl group, a pyrrolyl group, an imidazolyl group, a benzothienyl group, a benzofuranyl group, an indolyl group, a dibenzothienyl group, a dibenzofuranyl group, and a carbazolyl group. More preferable examples of the cyclic group include a phenyl group, a naphthyl group, a fluorenyl group, a phenanthrenyl group, a chrysenyl group, a pyridyl group, a pyrimidyl group, a thienyl group, a furanyl group, a pyrrolyl group, an imidazolyl group, a benzothienyl group, a benzofuranyl group, an indolyl group, a dibenzothienyl group, a dibenzofuranyl group, and a carbazolyl group, with a phenyl group, a naphthyl group, a fluorenyl group, a pyridyl group, a pyrimidyl group and benzothienyl group being further more preferable.

In addition, preferable examples of substituents for the cyclic groups include a halogen atom, an aryl group, a heteroaryl group, a linear or branched alkyl group, a linear or branched alkyl group which is substituted by a fluorine atom, an alkoxyl group, and a dialkylamino group. More preferable examples thereof include a fluorine atom, a methyl group, an ethyl group, a tertiary-butyl group, a trifluoromethyl group, a methoxy group, an ethoxy group, a dimethylamino group, a phenyl group, and a fluorenyl group, with a fluorine atom, a methyl group, a tertiary-butyl group and a methoxy group being further more preferable.

A ring structure B represents a 6- to 8-membered nonaromatic cyclic group having a nitrogen atom which is bonded to M, and may have at least one substituent selected from the group consisting of a halogen atom; a nitro group; an aryl group; a heteroaryl group; a dialkylamino group; a trialkylsilyl group having 1 to 8 carbon atoms; a linear or branched alkoxyl group having 1 to 20 carbon atoms in which one or unadjacent two or more methylene groups in the alkoxyl group may be replaced by at least one group selected from the group consisting of —O—, —S—, —CO—, —CO—O—, —O—CO—, —CH═CH— and —C≡C—, and one or two or more hydrogen atoms in the alkoxyl group may be substituted by a fluorine atom; and a linear or branched alkyl group having 1 to 20 carbon atoms in which one or unadjacent two or more methylene groups in the alkyl group may be substituted by at least one group selected from the group consisting of —O—, —S—, —CO—, —CO—O—, —O—CO—, —CH═CH— and —C≡C—, and one or two or more hydrogen atoms in the alkyl group may be substituted by a fluorine atom; provided that the substituents may be combined together to form a ring structure.

Preferable examples of the substituent include a halogen atom, an aryl group, a heteroaryl group, a linear or branched alkyl group, a linear or branched alkyl group in which one or two or more hydrogen atoms in the alkyl group are replaced by a fluorine atom, an alkoxyl group, and a dialkylamino group.

More preferable examples of the substituent include a fluorine atom, a phenyl group, a naphthyl group, a biphenyl group, a pyridyl group, a methyl group, an ethyl group, a tertiary-butyl group, a trifluoromethyl group, a methoxy group, an ethoxy group, a dimethylamino group, a phenyl group, a fluorenyl group, and a dialkylamino group.

Further more preferable examples of the substituent include a fluorine atom, a phenyl group, a methyl group, a tertiary-butyl group, a methoxy group, and a dialkylamino group.

In addition, $Y_1$ which forms the ring structure B represents an alkylene group having 4 to 6 carbon atoms in which one or unadjacent two or more methylene groups in the alkylene group may be replaced by at least one group selected from the group consisting of —O—, —CO—, —CO—O—, —O—CO—, —S—, and one of —CR$_1$═CR$_2$— and —NR$_3$— (where $R_1$ to $R_3$ are each independently a hydrogen atom, an aryl group, a heteroaryl group and a linear or branched alkyl group having 1 to 10 carbon atoms in which one or two or more hydrogen atoms in the alkyl group may be substituted by a fluorine atom, provided that the substituents may bind to each other to form a ring structure), and one or two or more hydrogen atoms in the alkylene group may be replaced by at least one of a fluorine atom and a linear or branched alkyl group having 1 to 10 carbon atoms in which one or two or more hydrogen atoms in the alkyl group may be substituted by a fluorine atom, provided that the substituents may be combined together to form a ring structure.

Preferable examples of a constituent unit of the alkylene group include —CR$_4$R$_5$— (where $R_4$ and $R_5$ each independently represent preferably any one of a hydrogen atom, a halogen atom, an aryl group, a linear or branched alkyl group having 1 to 10 carbon atoms in which one or two or more hydrogen atoms in the alkyl group may be replaced by a fluorine atom, and a linear or branched alkoxyl group having 1 to 10 carbon atoms in which one or two or more hydrogen atoms in the alkoxyl group may be replaced by a fluorine atom, and more preferably any one of a hydrogen atom, a fluorine atom, a phenyl group, a pyridyl group, a methyl group, a tertiary-butyl group, and a trifluoromethyl group, and further more preferably any one of a fluorine atom, a phenyl group, a hydrogen atom, and a trifluoromethyl group), —O—, —S—, —CR$_1$═CR$_2$— and —NR$_3$— (where $R_1$ to $R_3$ each independently represent preferably any one of a hydrogen atom, an aryl group, a heteroaryl group, and a linear or branched alkyl group having 1 to 10 carbon atoms in which one or two or more hydrogen atoms in the alkyl group may be replaced by a fluorine atom, more preferably any one of a phenyl group, a pyridyl group, a methyl group, a tertiary-butyl group, and a trifluoromethyl group, and further more preferably any one of a phenyl group, a methyl group, and a trifluoromethyl group), —CO—O—, —O—CO—, and —CO—.

More preferable examples of the constituent unit include —$CR_4R_5$— (where $R_4$ and $R_5$ each independently represent preferably any one of a hydrogen atom, a halogen atom, an aryl group, a heteroaryl group, a linear or branched alkyl group having 1 to 10 carbon atoms in which a hydrogen atom in the alkyl group may be substituted by a fluorine atom, and a linear or branched alkoxyl group having 1 to 10 carbon atoms in which one or two or more hydrogen atoms in the alkoxyl group may be replaced by a fluorine atom, more preferably any one of a hydrogen atom, a fluorine atom, a phenyl group, a pyridyl group, a methyl group, a tertiary-butyl group and a trifluoromethyl group, and further more preferably any one of a fluorine atom, a phenyl group, a hydrogen atom, and a trifluoromethyl group), —O—, —S—, —CO—, and —$CR_1$=$CR_2$— and —$NR_3$— (where $R_1$ to $R_3$ may each independently represent preferably any one of a hydrogen atom, an aryl group, a heteroaryl group, and a linear or branched alkyl group having 1 to 10 carbon atoms in which one or two or more hydrogen atoms in the alkyl group may be replaced by a fluorine atom, more preferably any one of a methyl group, a phenyl group, a pyridyl group, a tertiary-butyl group and a trifluoromethyl group, and further more preferably any one of a methyl group, a phenyl group, and a trifluoromethyl group.

Further more preferable examples of the constituent unit include —$CR_4R_5$— (where $R_4$ and $R_5$ may each independently represent preferably any one of a hydrogen atom, a halogen atom, an aryl group, a heteroaryl group, and a linear or branched alkyl group having 1 to 10 carbon atoms in which one or two or more hydrogen atoms in the alkyl group may be substituted by a fluorine atom, more preferably any one of a hydrogen atom, a fluorine atom, a methyl group, a tertiary-butyl group and a trifluoromethyl group, and further more preferably any one of a fluorine atom, a hydrogen atom, and a trifluoromethyl group), —$CR_1$=$CR_2$— and —$NR_3$— (where $R_1$ to $R_3$ each independently represent preferably any one of a hydrogen atom, an aryl group, a heteroaryl group, and a linear or branched alkyl group having 1 to 10 carbon atoms in which one or two or more hydrogen atoms in the alkyl group may be substituted by a fluorine atom, more preferably any one of a methyl group, a tertiary-butyl group and a trifluoromethyl group, and further more preferably one of a methyl group and a trifluoromethyl group), and —CO—.

In addition, in a case where a unit which forms $Y_1$ is formed from a carbon chain, the unit has no unpaired electron a hetero atom has, so that incorporation of ionic impurities may be reduced when such a unit is used, whereby the service life of a light-emitting device is expected to increase.

Accordingly, it is most desirable that $Y_1$ include one of —$CR_4R_5$— (where $R_4$ and $R_5$ each independently represent preferably any one of a hydrogen atom, an aryl group, a heteroaryl group, a halogen atom, or a linear or branched alkyl group having 1 to 10 carbon atoms in which one or two or more hydrogen atoms in the alkyl group may be replaced by a fluorine atom, more preferably any one of a hydrogen atom, a fluorine atom, a phenyl group, a pyridyl group, a methyl group, a tertiary-butyl group and a trifluoromethyl group, and further more preferably any one of a fluorine atom, a hydrogen atom, a phenyl group and a trifluoromethyl group), and —$CR_1$=$CR_2$— (where $R_1$ and $R_2$ each independently represent preferably any one of a hydrogen atom, an aryl group, a heteroaryl group, and a linear or branched alkyl group having 1 to 10 carbon atoms in which one or two or more hydrogen atoms in the alkyl group may be substituted by a fluorine atom, more preferably any one of a hydrogen atom, a phenyl group, a pyridyl group, a methyl group, a tertiary-butyl group and trifluoromethyl group, and further more preferably any one of a hydrogen atom, a phenyl group, a methyl group and a trifluoromethyl group).

The ring structure B which is formed from $Y_1$ is preferably a 6- to 8-membered ring, more preferably one of a 6-membered ring and a 7-membered ring, and further more preferably a 6-membered ring. This is because, when a complex is formed from a 6-membered ring, the distortion of a bond angle between the 6-membered ring and a metal atom may be reduced, and the 6-membered ring structure is thought to be most advantageous in stability of the structure of the complex.

A central metal of a metal complex is, but not particularly limited to, preferably any one of Ir, Pt, Rh, and Ru, more preferably one of Ir and Pt, and further more preferably Ir.

Next, each of the general formulae (2) to (4) is described having a ring structure formed by binding the substituents on the ring structure B, i.e. the substituents in $Y_1$, in the general formula (1).

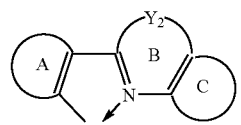

General Formula (2)

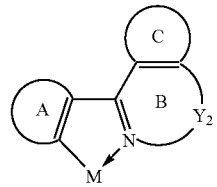

General Formula (3)

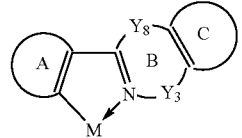

General Formula (4)

A ring structure A represents an aromatic cyclic group having a carbon atom which is bonded to M, and may have at least one substituent selected from the group consisting of a halogen atom; a nitro group; an aryl group; a heteroaryl group; a dialkylamino group; a trialkylsilyl group having 1 to 8 carbon atoms; a linear or branched alkoxyl group having 1 to 20 carbon atoms in which one or unadjacent two or more methylene groups in the alkoxyl group may be replaced by at least one group selected from the group consisting of —O—, —S—, —CO—, —CO—O—, —O—CO—, —CH=CH— and —C≡C—, and one or two or more hydrogen atoms in the alkoxyl group may be substituted by a fluorine atom; and a linear or branched alkyl group having 1 to 20 carbon atoms in which one or unadjacent methylene groups in the alkyl group may be replaced by at least one group selected from the group consisting of —O—, —S—, —CO—, —CO—O—, —O—CO—, —CH=CH— and —C≡C—, and one or two or more hydrogen atoms in the alkyl group may be substituted by a fluorine atom; provided that the substituents may be combined together to form a ring structure.

The ring structure A is an aromatic cyclic group having a carbon atom which is bonded to M. Examples of the cyclic group include a phenyl group, a naphthyl group, an anthranyl group, a fluorenyl group, a pyrenyl group, a phenanthrenyl group, a chrysenyl group, a fluoranthenyl group, a triphenylenyl group, a perylenyl group, a pyridyl group, a pyrazinyl group, a pyrimidyl group, a pyridazinyl group, a quinolinyl group, an isoquinolinyl group, a phenanthridinyl group, an acridinyl group, a naphthyridinyl group, a quinoxalinyl group, a quinazolinyl group, a cinnolinyl group, a phthalazinyl group, a phenanthrolyl group, a phenazinyl group, a thiazolyl group, a thienyl group, a furanyl group, a pyrrolyl group, an imidazolyl group, a benzothienyl group, a benzofuranyl group, an indolyl group, a dibenzothienyl group, a dibenzofuranyl group, and a carbazolyl group. Preferable examples of the cyclic group include a phenyl group, a naphthyl group, an anthranyl group, a fluorenyl group, a phenanthrenyl group, a chrysenyl group, a triphenylenyl group, a pyridyl group, a pyrazinyl group, a pyrimidyl group, a pyridazinyl group, a quinolinyl group, an isoquinolinyl group, a naphthyridinyl group, a quinoxalinyl group, a thienyl group, a furanyl group, a pyrrolyl group, an imidazolyl group, a benzothienyl group, a benzofuranyl group, an indolyl group, a dibenzothienyl group, a dibenzofuranyl group, and a carbazolyl group. More preferable examples of the cyclic group include a phenyl group, a naphthyl group, a fluorenyl group, a phenanthrenyl group, a chrysenyl group, a pyridyl group, a pyrimidyl group, a thienyl group, a furanyl group, a pyrrolyl group, an imidazolyl group, a benzothienyl group, a benzofuranyl group, an indolyl group, a dibenzothienyl group, a dibenzofuranyl group, and a carbazolyl group, with a phenyl group, a naphthyl group, a fluorenyl group, a pyridyl group, a pyrimidyl group, and benzothienyl group being further more preferable.

In addition, preferable examples of substituents for the cyclic groups include a halogen atom, an aryl group, a heteroaryl group, a linear or branched alkyl group, a linear or branched alkyl group in which one or two or more hydrogen atoms in the alkyl may be replaced by a fluorine atom, an alkoxyl group, and a dialkylamino group. More preferable examples thereof include a fluorine atom, a methyl group, an ethyl group, a tertiary-butyl group, a trifluoromethyl group, a methoxy group, an ethoxy group, a dimethylamino group, a phenyl group, and a fluorenyl group, with a fluorine atom, a methyl group, a tertiary-butyl group and a methoxy group being further more preferable.

A ring structure B represents a 6- to 8-membered non-aromatic cyclic group having a nitrogen atom which is bonded to M, and may have at least one substituent selected from the group consisting of a halogen atom; a nitro group; an aryl group; a heteroaryl group; a dialkylamino group; a trialkylsilyl group having 1 to 8 carbon atoms; a linear or branched alkoxyl group having 1 to 20 carbon atoms in which one or unadjacent two or more methylene groups in the alkoxyl group may be replaced by at least one group selected from the group consisting of —O—, —S—, —CO—, —CO—O—, —O—CO—, —CH=CH— and —C≡C—, and one or two or more hydrogen atoms in the alkoxyl group may be substituted by a fluorine atom; and a linear or branched alkyl group having 1 to 20 carbon atoms in which one or unadjacent two or more methylene groups in the alkyl group may be substituted by at least one group selected from the group consisting of —O—, —S—, —CO—, —CO—O—, —O—CO—, —CH=CH—, and —C≡C— and one or two or more hydrogen atoms in the alkyl group may be replaced by a fluorine atom; provided that the substituents may be combined together to form a ring structure.

Preferable examples of the substituent include a halogen atom, an aryl group, a heteroaryl group, a linear or branched alkyl group, a linear or branched alkyl group in which one or two or more hydrogen atoms in the alkyl may be replaced by a fluorine atom, an alkoxyl group, and a dialkylamino group. More preferable examples of the substituent include a fluorine atom, a phenyl group, a naphthyl group, a biphenyl group, a pyridyl group, a methyl group, an ethyl group, a tertiary-butyl group, a trifluoromethyl group, a methoxy group, an ethoxy group, a dimethylamino group, a phenyl group, a fluorenyl group, and a dialkylamino group. Further more preferable examples of the substituent include a fluorine atom, a phenyl group, a methyl group, a tertiary-butyl group, a methoxy group, and a dialkylamino group.

In addition, $Y_2$ which forms the ring structure B of the general formulae (2) and (3) represents an alkylene group having 2 to 4 carbon atoms in which one or two methylene groups in the alkylene group may be replaced by at least one group selected from the group consisting of —O—, —CO—, —CO—O—, —O—CO—, —S—, and one of —$CR_1$=$CR_2$— and —$NR_3$— (where $R_1$ to $R_3$ are each independently a hydrogen atom, an aryl group, a heteroaryl group, and a linear or branched alkyl group having 1 to 10 carbon atoms in which one or two or more hydrogen atoms in the alkyl group may be replaced by a fluorine atom, provided that the substituents may be combined together to form a ring structure), and one or two or more hydrogen atoms in the alkylene group may be replaced by at least one of a fluorine atom and a linear or branched alkyl group having 1 to 10 carbon atoms in which one or two or more hydrogen atoms in the alkyl group may be substituted by a fluorine atom, provided that the substituents may be combined together to form a ring structure.

Preferable examples of a constituent unit of the alkylene group include —$CR_4R_5$— (where $R_4$ and $R_5$ each independently represent preferably any one of a hydrogen atom, a halogen atom, an aryl group, a linear or branched alkyl group having 1 to 10 carbon atoms in which one or more hydrogen atoms in the alkyl group may be replaced by a fluorine atom, and a linear or branched alkoxyl group having 1 to 10 carbon atoms in which one or two or more hydrogen atoms in the alkoxyl group may be substituted by a fluorine atom, more preferably any one of a hydrogen atom, a fluorine atom, a phenyl group, a pyridyl group, a methyl group, a tertiary-butyl group and a trifluoromethyl group, and further more preferably any one of a fluorine atom, a phenyl group, a hydrogen atom, and a trifluoromethyl group), —O—, —S—, —$CR_1$=$CR_2$— and —$NR_3$— (where $R_1$ to $R_3$ each independently represent preferably any one of a hydrogen atom, an aryl group, a heteroaryl group, and a linear or branched alkyl group having 1 to 10 carbon atoms in which one or two or more hydrogen atoms in the alkyl group may be replaced by a fluorine atom, more preferably any one of a phenyl group, a pyridyl group, a methyl group, a tertiary-butyl group, and a trifluoromethyl group, and further more preferably any one of a phenyl group, a methyl group, and a trifluoromethyl group), —CO—O—, —O—CO—, and —CO—.

More preferable examples of the constituent unit include —$CR_4R_5$— (where $R_4$ and $R_5$ each independently represent preferably any one of a hydrogen atom, a halogen atom, an aryl group, a heteroaryl group, a linear or branched alkyl group having 1 to 10 carbon atoms in which one or two or more hydrogen atoms in the alkyl group may be replaced by a fluorine atom, and a linear or branched alkoxyl group having 1 to 10 carbon atoms in which one or two or more hydrogen atoms in the alkoxyl group may be replaced by a fluorine atom, more preferably any one of a hydrogen atom, a fluorine atom, a phenyl group, a pyridyl group, a methyl group, a tertiary-butyl group, and a trifluoromethyl group, and further more preferably any one of a fluorine atom, a phenyl group, a hydrogen atom, and a trifluoromethyl group), —O—, —S—, —CO—, and —CR$_1$=CR$_2$— and —NR$_3$— (where R$_1$ to R$_3$ each independently represent preferably any one of a hydrogen atom, an aryl group, a heteroaryl group, and a linear or branched alkyl group having 1 to 10 carbon atoms in which one or two or more hydrogen atoms in the alkyl group may be replaced by a fluorine atom, more preferably any one of a methyl group, a phenyl group, a pyridyl group, a tertiary-butyl group, and a trifluoromethyl group, and more preferably any one of a methyl group, a phenyl group, and a trifluoromethyl group).

Further more preferable examples of the constituent unit include —CR$_4$R$_5$— (where R$_4$ and R$_5$ each independently represent preferably any one of a hydrogen atom, a halogen atom, an aryl group, a heteroaryl group, and a linear or branched alkyl group having 1 to 10 carbon atoms in which one or two or more hydrogen atoms in the alkyl group may be replaced by a fluorine atom, more preferably any one of a hydrogen atom, a fluorine atom, a methyl group, a tertiary-butyl group and a trifluoromethyl group, and further more preferably any one of a fluorine atom, a hydrogen atom, and a trifluoromethyl group), —CR$_1$=CR$_2$— and —NR$_3$— (where R$_1$ to R$_3$ each independently represent preferably any one of a hydrogen atom, an aryl group, a heteroaryl group, and a linear or branched alkyl group having 1 to 10 carbon atoms in which one or two or more hydrogen atoms in the alkyl group may be substituted by a fluorine atom, more preferably any one of a methyl group, a tertiary-butyl group, and a trifluoromethyl group, and further more preferably one of a methyl group and a trifluoromethyl group), and —CO—.

In addition, in a case where a unit which forms Y$_2$ is formed from a carbon chain, the unit has no unpaired electron that a hetero atom has, so that incorporation of ionic impurities may be reduced when such a unit is used, whereby the service life of a light-emitting device is expected to increase.

Accordingly, it is most desirable that Y$_2$ include —CR$_4$R$_5$— (where R$_4$ and R$_5$ each independently represent preferably a hydrogen atom, an aryl group, a heteroaryl group, a halogen atom, a linear or branched alkyl group having 1 to 10 carbon atoms in which one or two or more hydrogen atoms in the alkyl group may be replaced by a fluorine atom, more preferably any one of a hydrogen atom, a fluorine atom, a phenyl group, a pyridyl group, a methyl group, a tertiary-butyl group, and a trifluoromethyl group, and further more preferably any one of a fluorine atom, a hydrogen atom, a phenyl group, and a trifluoromethyl group), or —CR$_1$=CR$_2$— (where R$_1$ and R$_2$ each independently represent preferably any one of a hydrogen atom, an aryl group, a heteroaryl group, and a linear or branched alkyl group having 1 to 10 carbon atoms in which one or more hydrogen atom in the alkyl group may be replaced by a fluorine atom, more preferably any one of a hydrogen atom, a phenyl group, a pyridyl group, a methyl group, a tertiary-butyl group, and trifluoromethyl group, and further more preferably any one of a hydrogen atom, a phenyl group, a methyl group, and a trifluoromethyl group).

The ring structure B which is formed from Y$_2$ is preferably a 6- to 8-membered ring, more preferably a 6-membered ring or a 7-membered ring, and further more preferably a 6-membered ring. This is because, when a complex is formed from a 6-membered ring, distortion of a bond angle between the 6-membered ring and a metal atom may be reduced, and the 6-membered ring structure is thought to be most advantageous in stability of the structure of the complex.

In addition, Y$_3$ which forms the ring structure B of the general formula (4) represents an alkylene group having 1 to 3 carbon atoms, provided that two Y$_3$'s have 2 to 4 carbon atoms in total, in which one or two methylene groups in the alkylene group may be substituted by at least one group selected from the group consisting of —O—, —CO—, —CO—O—, —O—CO—, —S—, and one of —CR$_1$=CR$_2$— and —NR$_3$— (where R$_1$ to R$_3$ are each independently any one of a hydrogen atom, an aryl group, a heteroaryl group, and a linear or branched alkyl group having 1 to 10 carbon atoms in which one or two or more hydrogen atoms in the alkyl group may be replaced by a fluorine atom, provided that the substituents may be combined together to form a ring structure), and one or two or more hydrogen atoms in the alkylene group may be replaced by at least one of a fluorine atom and a linear or branched alkyl group having 1 to 10 carbon atoms in which one or two or more hydrogen atoms in the alkyl group may be replaced by a fluorine atom; provided that the substituents may be combined together to form a ring structure.

Preferable examples of a constituent unit of the alkylene group include —CR$_4$R$_5$— (where R$_4$ and R$_5$ each independently represent preferably any one of a hydrogen atom, a halogen atom, an aryl group, a linear or branched alkyl group having 1 to 10 carbon atoms in which one or two or more hydrogen atoms in the alkyl group may be replaced by a fluorine atom, and a linear or branched alkoxyl group having 1 to 10 carbon atoms in which one or two or more hydrogen atom in the alkoxyl group may be replaced by a fluorine atom, more preferably any one of a hydrogen atom, a fluorine atom, a phenyl group, a pyridyl group, a methyl group, a tertiary-butyl group, and a trifluoromethyl group, and further more preferably any one of a fluorine atom, a phenyl group, a hydrogen atom, and a trifluoromethyl group), —O—, —S—, —CR$_1$=CR$_2$— and —NR$_3$— (where R$_1$ to R$_3$ each independently represent preferably any one of a hydrogen atom, an aryl group, a heteroaryl group, and a linear or branched alkyl group having 1 to 10 carbon atoms in which one or two or more hydrogen atoms in the alkyl group may be replaced by a fluorine atom, more preferably any one of a phenyl group, a pyridyl group, a methyl group, a tertiary-butyl group, and a trifluoromethyl group, and further more preferably any one of a phenyl group, a methyl group, and a trifluoromethyl group), —CO—O—, —O—CO—, and —CO—.

More preferable examples of the constituent unit include —CR$_4$R$_5$— (where R$_4$ and R$_5$ each independently represent preferably any one of a hydrogen atom, a halogen atom, an aryl group, a heteroaryl group, a linear or branched alkyl group having 1 to 10 carbon atoms in which one or two or more hydrogen atoms in the alkyl group may be replaced by a fluorine atom, and a linear or branched alkoxyl group having 1 to 10 carbon atoms in which one or two or more hydrogen atoms in the alkoxyl group may be replaced by a fluorine atom, more preferably any one of a hydrogen atom, a fluorine atom, a phenyl group, a pyridyl group, a methyl group, a tertiary-butyl group, and a trifluoromethyl group, and further more preferably any one of a fluorine atom, a phenyl group, a hydrogen atom, and a trifluoromethyl group), —O—, —S—, —CO—, and —CR$_1$=CR$_2$— and —NR$_3$— (where R$_1$ to R$_3$ each independently represent preferably any one of a hydrogen atom, an aryl group, a heteroaryl group, and a linear or branched alkyl group having 1 to 10 carbon atoms in which one or two or more hydrogen atoms in the alkyl group may be replaced by a fluorine atom, more preferably any one of a methyl group, a phenyl group, a pyridyl group, a tertiary-butyl group, and a trifluoromethyl group, and further more preferably any one of a methyl group, a phenyl group, and a trifluoromethyl group.

Further more preferable examples of the constituent unit include —$CR_4R_5$— (where $R_4$ and $R_5$ each independently represent preferably any one of a hydrogen atom, a halogen atom, an aryl group, a heteroaryl group, and a linear or branched alkyl group having 1 to 10 carbon atoms in which one or two or more hydrogen atoms in the alkyl group may be replaced by a fluorine atom, more preferably any one of a hydrogen atom, a fluorine atom, a methyl group, a tertiary-butyl group, and a trifluoromethyl group, and further more preferably any one of a fluorine atom, a hydrogen atom, and a trifluoromethyl group), —$CR_1$=$CR_2$— and —$NR_3$— (where $R_1$ to $R_3$ each independently represent preferably any one of a hydrogen atom, an aryl group, a heteroaryl group, and a linear or branched alkyl group having 1 to 10 carbon atoms in which one or two or more hydrogen atoms in the alkyl group may be replaced by a fluorine atom, more preferably any one of a methyl group, a tertiary-butyl group, and a trifluoromethyl group, and further more preferably one of a methyl group and a trifluoromethyl group), and —CO—.

In addition, in a case where a unit which forms $Y_3$ is formed from a carbon chain, the unit has no unpaired electron that a hetero atom has, so that incorporation of ionic impurities may be reduced when such a unit is used, whereby the service life of a light-emitting device is expected to increase.

Accordingly, it is most desirable that $Y_3$ include —$CR_4R_5$— (where $R_4$ and $R_5$ each independently represent preferably a hydrogen atom, an aryl group, a heteroaryl group, a halogen atom, a linear or branched alkyl group having 1 to 10 carbon atoms in which one or two or more hydrogen atoms in the alkyl group may be replaced by a fluorine atom, more preferably any one of a hydrogen atom, a fluorine atom, a phenyl group, a pyridyl group, a methyl group, a tertiary-butyl group, and a trifluoromethyl group, and further more preferably any one of a fluorine atom, a hydrogen atom, a phenyl group, and a trifluoromethyl group), or —$CR_1$=$CR_2$— (in which $R_1$ and $R_2$ each independently represent preferably any one of a hydrogen atom, an aryl group, a heteroaryl group, and a linear or branched alkyl group having 1 to 10 carbon atoms in which one or two or more hydrogen atoms in the alkyl group may be replaced by a fluorine atom, more preferably any one of a hydrogen atom, a phenyl group, a pyridyl group, a methyl group, a tertiary-butyl group, and trifluoromethyl group, and further more preferably any one of a hydrogen atom, a phenyl group, a methyl group, and a trifluoromethyl group).

The ring structure B which is formed from $Y_3$ is preferably a 6- to 8-membered ring, more preferably one of a 6-membered ring and a 7-membered ring, and further more preferably a 6-membered ring. This is because, when a complex is formed of a 6-membered ring, distortion of a bond angle between the 6-membered ring and a metal atom may be reduced, and the 6-membered structure is thought to be most advantageous in stability of the structure of the complex.

A ring structure C represents an aromatic cyclic group condensed with the ring structure B, and may have at least one substituent selected from the group consisting of a halogen atom; a nitro group; an aryl group; a heteroaryl group; a dialkylamino group; a trialkylsilyl group having 1 to 8 carbon atoms; a linear or branched alkoxyl group having 1 to 20 carbon atoms in which one or unadjacent two or more methylene groups in the alkoxyl group may be replaced by at least one group selected from the group consisting of —O—, —S—, —CO—, —CO—O—, —O—CO—, —CH=CH— and —C≡C—, and one or two or more hydrogen atoms in the alkoxyl group may be substituted by a fluorine atom; and a linear or branched alkyl group having 1 to 20 carbon atoms in which one or unadjacent two or more methylene groups in the alkyl group may be replaced by at least one group selected from the group consisting of —O—, —S—, —CO—, —CO—O—, —O—CO—, —CH=CH— and —C≡C—, and one or two or more hydrogen atoms in the alkyl group may be replaced by a fluorine atom, provided that the substituents may be combined together to form a ring structure.

Examples of a cyclic group which forms the ring structure C include a phenyl group, a naphthyl group, an anthranyl group, a fluorenyl group, a pyrenyl group, a phenanthrenyl group, a chrysenyl group, a fluoranthenyl group, a triphenylenyl group, a perylenyl group, a pyridyl group, a pyrazinyl group, a pyrimidyl group, a pyridazinyl group, a quinolinyl group, an isoquinolinyl group, a phenanthridinyl group, an acridinyl group, a naphthyridinyl group, a quinoxalinyl group, a quinazolinyl group, a cinnolinyl group, a phthalazinyl group, a phenanthrolyl group, a phenazinyl group, a thiazolyl group, a thienyl group, a furanyl group, a pyrrolyl group, an imidazolyl group, a benzothienyl group, a benzofuranyl group, an indolyl group, a dibenzothienyl group, a dibenzofuranyl group, and a carbazolyl group.

Preferable examples of the cyclic group include a phenyl group, a naphthyl group, an anthranyl group, a fluorenyl group, a phenanthrenyl group, a triphenylenyl group, a pyridyl group, a pyrazinyl group, a pyrimidyl group, a pyridazinyl group, a quinolinyl group, an isoquinolinyl group, a naphthyridinyl group, and a quinoxalinyl group.

More preferable examples of the cyclic group include a phenyl group, a naphthyl group, a phenanthrenyl group, a triphenylenyl group, a pyridyl group, a pyrazinyl group, a pyrimidyl group, a quinolinyl group, and a quinoxalinyl group, and particularly preferable examples thereof include a phenyl group, a naphthyl group, and a pyridyl group.

In addition, preferable examples of a substituent for the cyclic groups include a halogen atom, an aryl group, a heteroaryl group, a linear or branched alkyl group, a linear or branched alkyl group in which one or two or more hydrogen atoms in the alkyl group are replaced by a fluorine atom, an alkoxyl group, and a dialkylamino group. More preferable examples thereof include a fluorine atom, a methyl group, an ethyl group, a tertiary-butyl group, a trifluoromethyl group, a methoxy group, an ethoxy group, a dimethylamino group, a phenyl group, and a fluorenyl group.

Further more preferable examples of the substituent for the cyclic groups include a fluorine atom, a methyl group, a tertiary-butyl group, and a methoxy group. The central metal of the metal complex is, but not particularly limited to, preferably any one of Ir, Pt, Rh, and Ru, more preferably one of Ir and Pt, and further more preferably Ir.

The more specific structure of the general formula (5) will be described below.

$$ML1_mL2_n \qquad \text{General Formula (5)}$$

In the general formula (5), L1 and L2 represent bidentate ligands different from each other, m represents 1, 2 or 3, and n represents 0, 1 or 2, provided that m+n is 2 or 3.

A partial structure ML1 is represented by the general formula (1) as mentioned above, and a partial structure ML2 is represented by any one of the general formulae (6), (7), and (8).

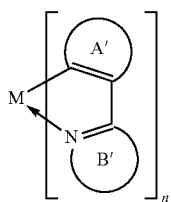

General Formula (6)

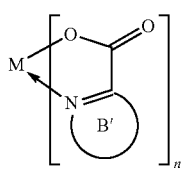

General Formula (7)

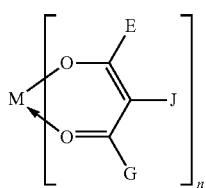

General Formula (8)

N represents a nitrogen atom, A' represents a cyclic group which may be substituted, and is bonded to a metal atom M via a carbon atom, and B' represents a cyclic group which may be substituted, and is bonded to a metal atom M via a nitrogen atom, each of A' and B' being bonded by covalent bond.

The cyclic group A' represents preferably any one of a phenyl group, a naphthyl group, a fluorenyl group, a thienyl group, a benzothienyl group, and a benzofuranyl group, and more preferably a phenyl group.

Preferable examples of substituents for the cyclic groups include a halogen atom, a linear or branched alkyl group, a linear or branched alkyl group which is thoroughly or partially substituted by a fluorine atom, an alkoxyl group, a dialkylamino group, and a cyano group.

More preferable examples of substituents for the cyclic groups include a fluorine atom, a methyl group, a trifluoromethyl group, a methoxy group, and a cyano group, and further more preferable examples thereof include a fluorine atom, a methyl group, and a cyano group.

Preferable examples of the cyclic group B' include a pyridyl group, a pyrazinyl group, a pyrimidyl group, a pyridazinyl group, a triazinyl group, a quinolinyl group, an isoquinolinyl group, a phenanthridinyl group, an acridinyl group, a naphthyridinyl group, a quinoxalinyl group, a quinazolinyl group, a cinnolinyl group, a phthalazinyl group, a phenanthrolyl group, a thiazolyl group, an isothiazolyl group, an imidazolyl group, a pyrazolyl group, an oxazolyl group, an isoxazolyl group, a benzothiazolyl group, a benzisothiazolyl group, a benzimidazolyl group, a benzopyrazolyl group, benzoxazolyl group, and a benzoisoxazolyl group.

More preferable examples thereof include a pyridyl group, a pyrazinyl group, a pyrimidyl group, a triazinyl group, a quinolinyl group, an isoquinolinyl group, a quinoxalinyl group, a phenanthrolyl group, a thiazolyl group, an isothiazolyl group, an imidazolyl group, a pyrazolyl group, an oxazolyl group, and an isoxazolyl group.

Further more preferable examples thereof include a pyridyl group, an imidazolyl group, a pyrazolyl group, and an isoquinolinyl group.

Preferable examples of substituents for the cyclic group include a halogen atom, a linear or branched alkyl group, a linear or branched alkyl group which is thoroughly or partially substituted by a fluorine atom, an alkoxyl group, and a dialkylamino group.

More preferable examples of substituents for the cyclic groups include a fluorine atom, a methyl group, an ethyl group, a trifluoromethyl group, a methoxy group, an ethoxy group, and a dimethylamino group.

E and G each independently represent one of a linear or branched alkyl group having 1 to 20 carbon atoms in which one or unadjacent two or more methylene groups in the alkyl group may be replaced by at least one group selected from the group consisting of —O—, —S—, —CO—, —CO—O—, —O—CO—, —CH═CH— and —C≡C—, and one or two or more hydrogen atoms in the alkyl group may be replaced by a fluorine atom; and an aromatic cyclic group which may have at least one substituent selected from the group consisting of a halogen atom, a cyano group, a nitro group, a trialkylsilyl group whose alkyl groups are each independently a linear or branched alkyl group having 1 to 8 carbon atoms, and a linear or branched alkyl group having 1 to 20 carbon atoms in which one or unadjacent two or more methylene groups in the alkyl group may be replaced by at least one group selected from the group consisting of —O—, —S—, —CO—, —CO—O—, —O—CO—, —CH═CH— and —C≡C—, and one or two or more hydrogen atoms in the alkyl group may be replaced by a fluorine atom.

E and G each independently represent preferably any one of a methyl group, a tertiary-butyl group, a trifluoromethyl group, a methoxy group, an ethoxy group, and a phenyl group, and more preferably any one of a methyl group, a tertiary-butyl group, and a methoxy group.

J represents any one of a hydrogen atom; a halogen atom; a linear or branched alkyl group having 1 to 20 carbon atoms in which one or two or more hydrogen atoms in the alkyl group may be replaced by a fluorine atom; and an aromatic cyclic group which may have at least one substituent selected from the group consisting of a halogen atom, a cyano group, a nitro group, a trialkylsilyl group whose alkyl groups are each independently a linear or branched alkyl group having 1 to 8 carbon atoms, and a linear or branched alkyl group having 1 to 20 carbon atoms in which one or unadjacent two or more methylene groups in the alkyl group may be replaced by at least one group selected from the group consisting of —O—, —S—, —CO—, —CO—O—, —O—CO—, —CH═CH— and —C≡C—, and one or two or more hydrogen atoms in the alkyl group may be replaced by a fluorine atom.

J represents preferably any one of a hydrogen atom, a methyl group, a trifluoromethyl group, a methoxy group, an ethoxy group, and a phenyl group, and more preferably one of a hydrogen atom and a methyl group.

The central metal of the metal complex is, but not particularly limited to, preferably any one of Ir, Pt, Rh, and Ru, more preferably one of Ir and Pt, and further more preferably Ir.

Next, the general formula (9) will be described.

$$ML3_mL4_n \qquad \text{General Formula (9)}$$

In the general formula (9), L3 and L4 represent bidentate ligands different from each other, m represents 1, 2 or 3, and n represents 1, 2 or 3, provided that m+n is 2 or 3.

A partial structure $ML3_m$ is represented by any one of the general formulae (2), (3), and (4) as mentioned above. A partial structure $ML4_n$ is represented by any one of the general formulae (6), (7), and (8) as mentioned above.

The central metal of the metal complex is, but not particularly limited to, preferably any one of Ir, Pt, Rh, and Ru, more preferably one of Ir and Pt, and further more preferably Ir.

Hereinafter, specific examples of the metal coordination compound of the present invention are shown. However, they only show typical examples of the present invention, and the present invention is not limited thereto.

General Formula (12)

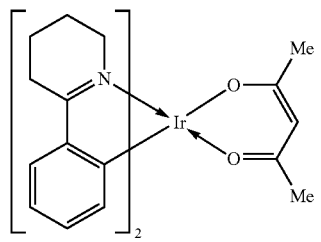

XA-1

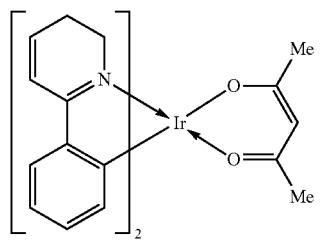

XA-2

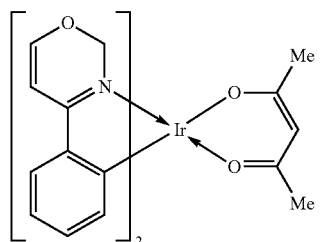

XA-3

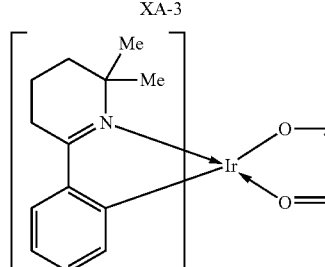

XA-4

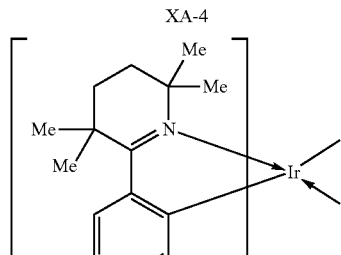

XA-5

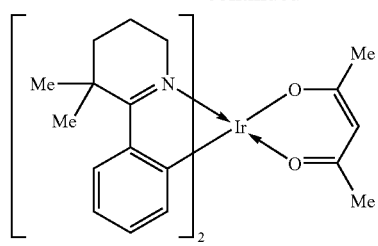

XA-6

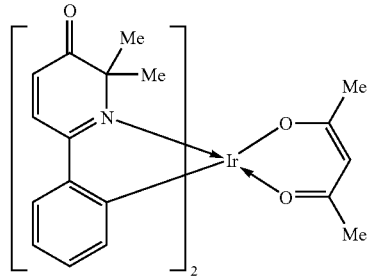

XA-7

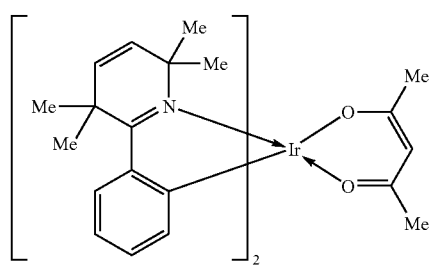

XA-8

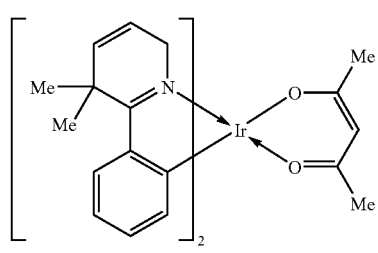

XA-9

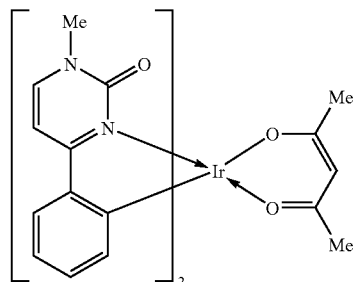

XA-10

-continued
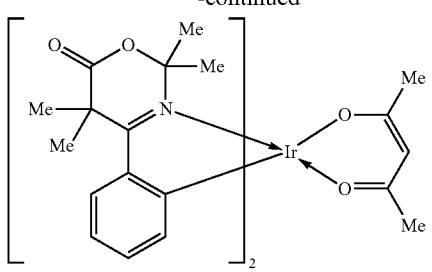
XA-11
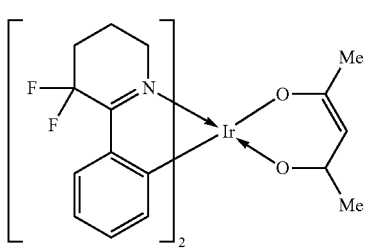
XA-12
General Formula (13)
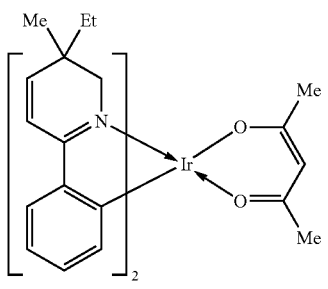
XA-13
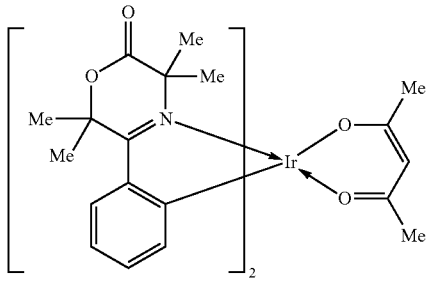
XA-14
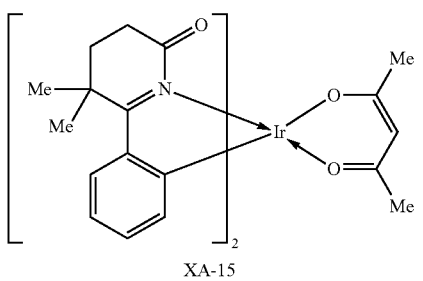
XA-15
-continued
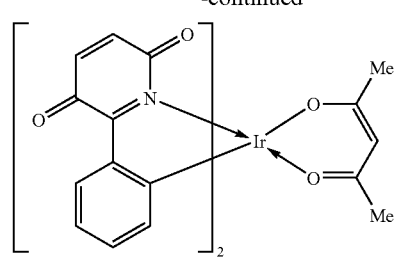
XA-16
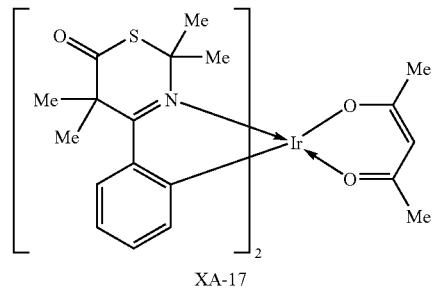
XA-17
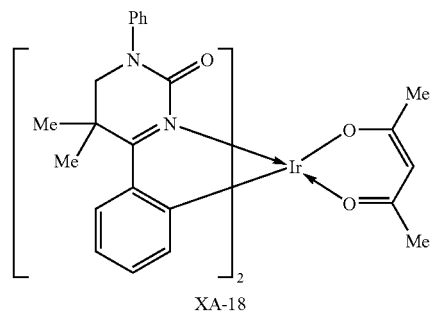
XA-18
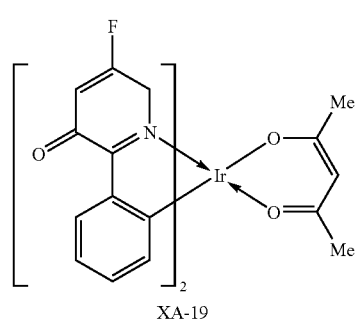
XA-19
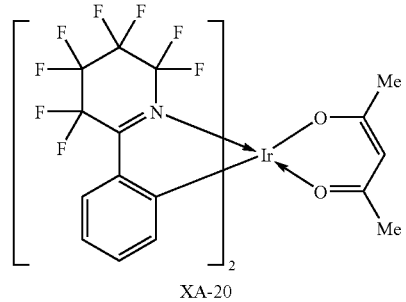
XA-20

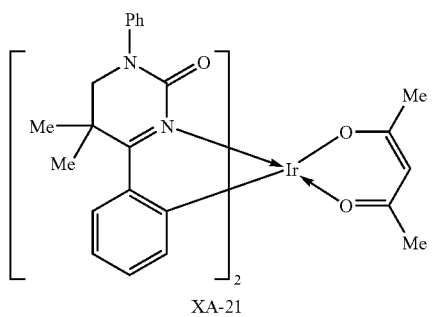

-continued
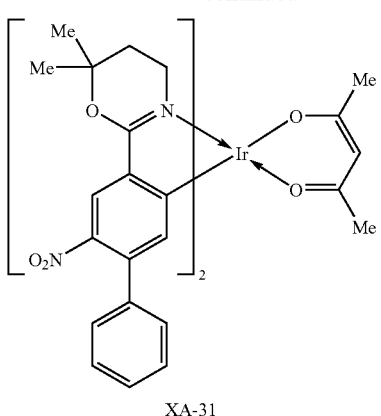
XA-31
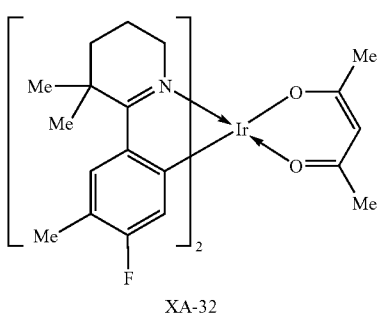
XA-32
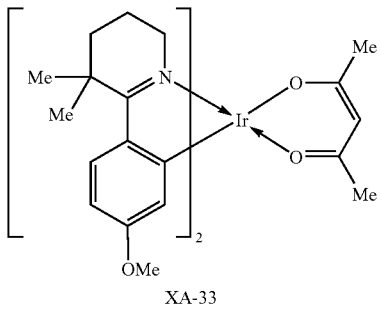
XA-33
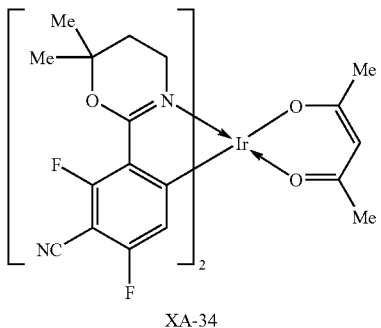
XA-34
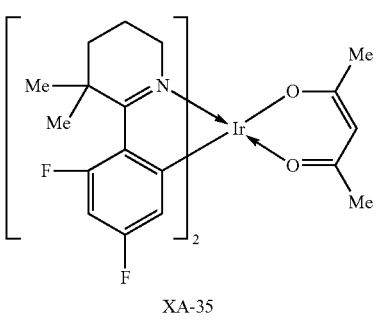
XA-35
-continued
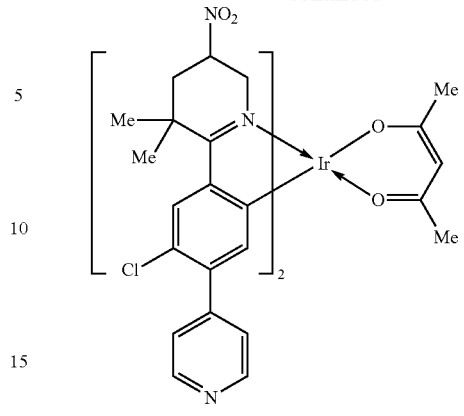
XA-36
General Formula (15)
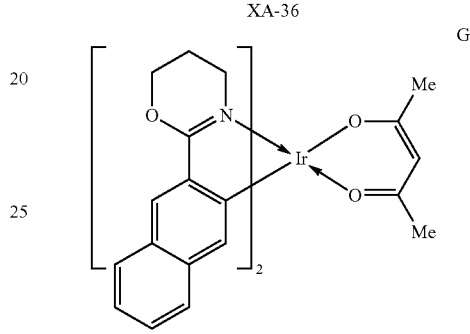
XA-37
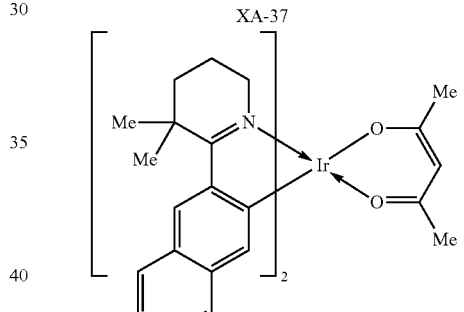
XA-38
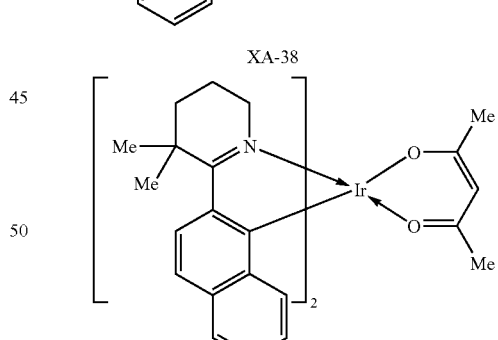
XA-39
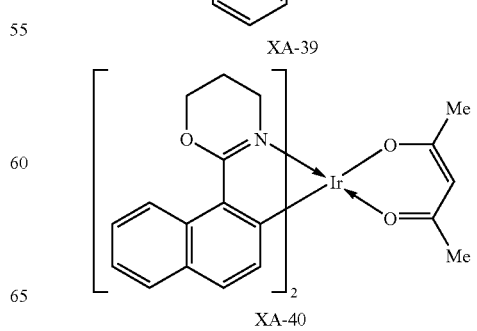
XA-40

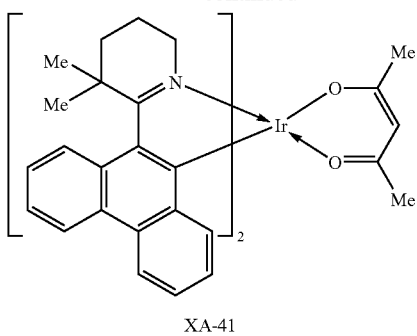
XA-41
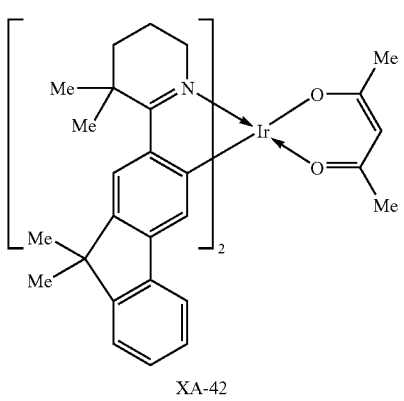
XA-42
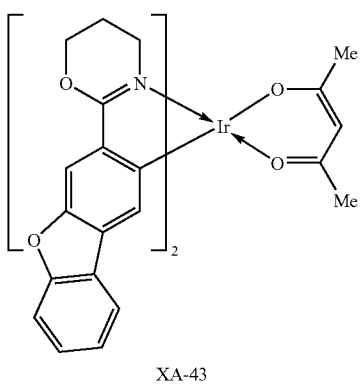
XA-43
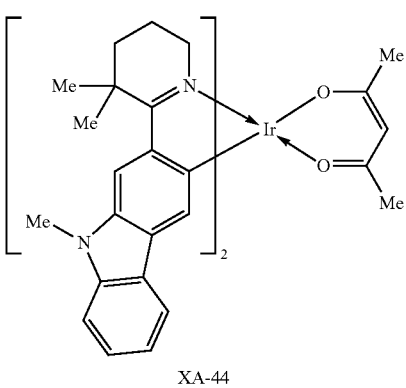
XA-44
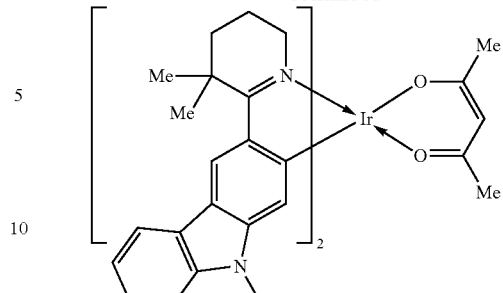
XA-45
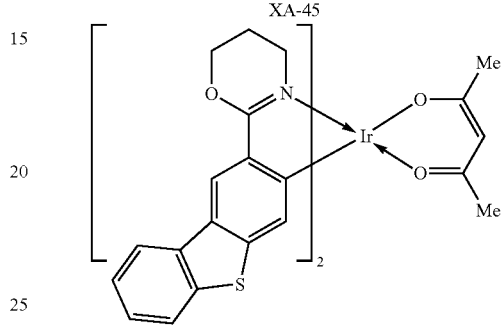
XA-46
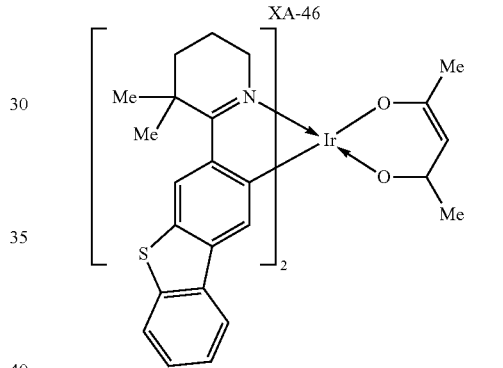
XA-47
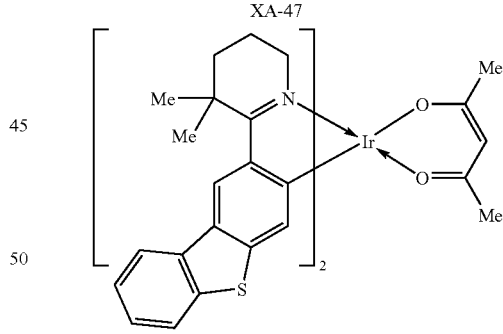
XA-48
General Formula (16)
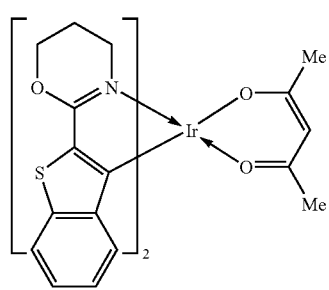
XA-49

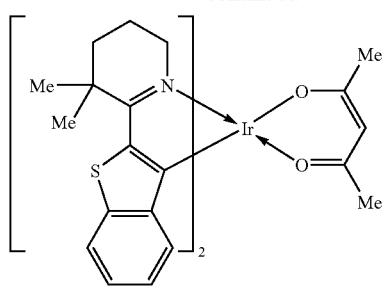
XA-50
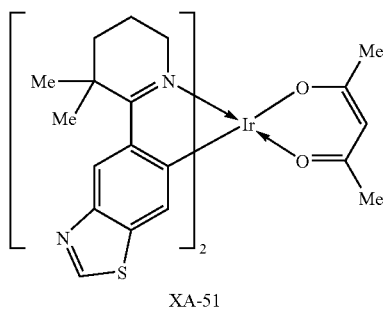
XA-51
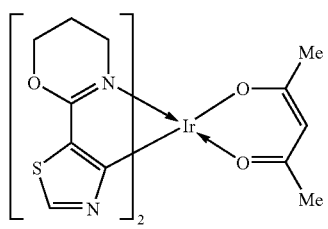
XA-52
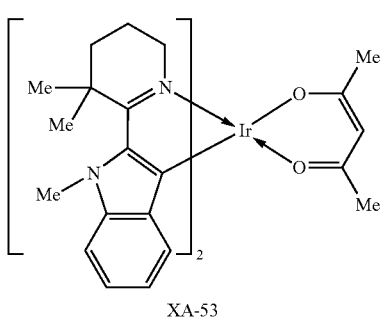
XA-53
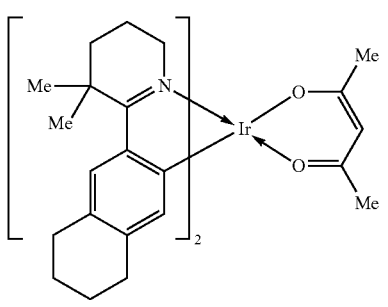
XA-54
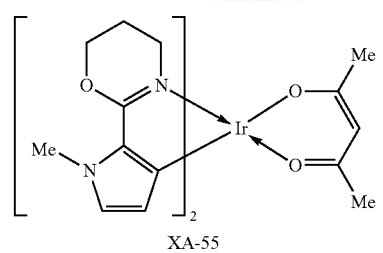
XA-55
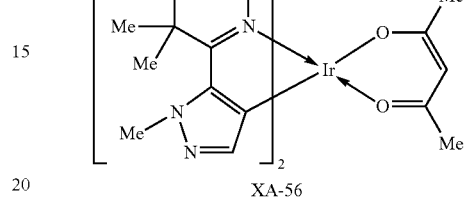
XA-56
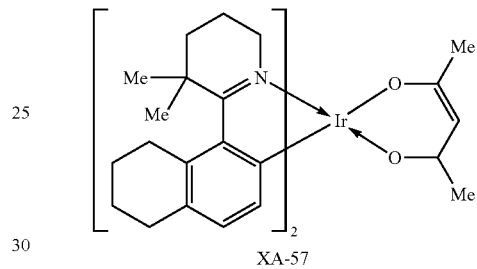
XA-57
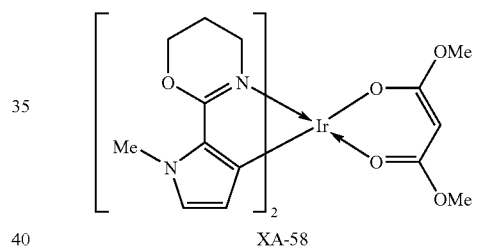
XA-58
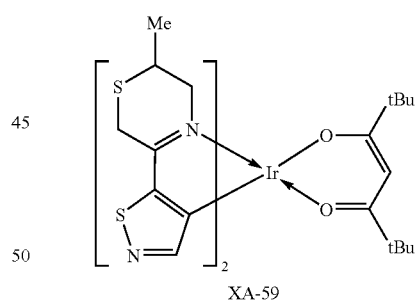
XA-59
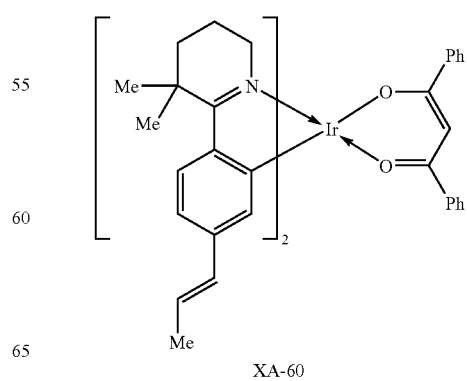
XA-60

General Formula (17)
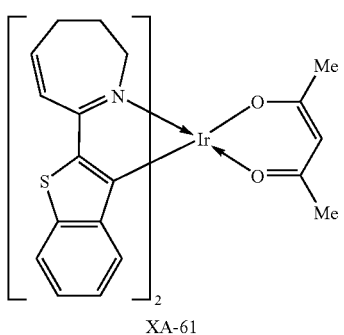
XA-61
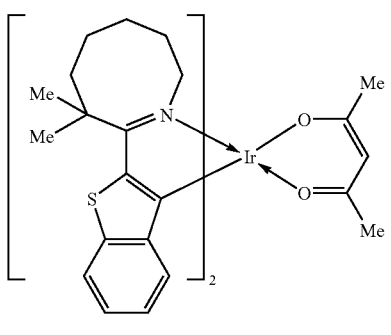
XA-62
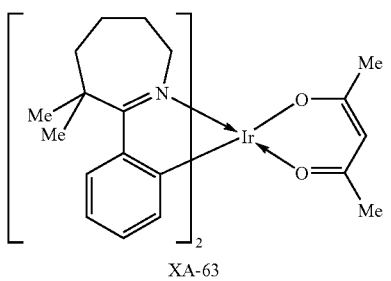
XA-63
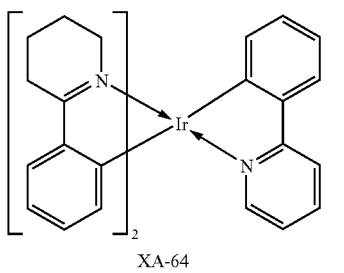
XA-64
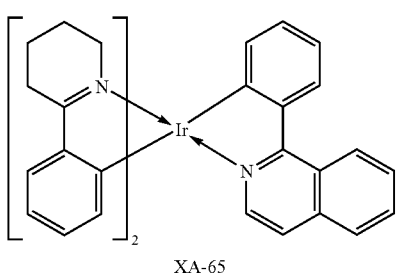
XA-65
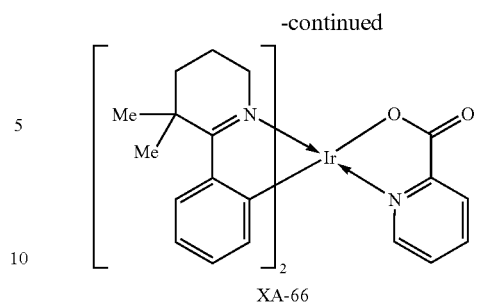
XA-66
General Formula (18)
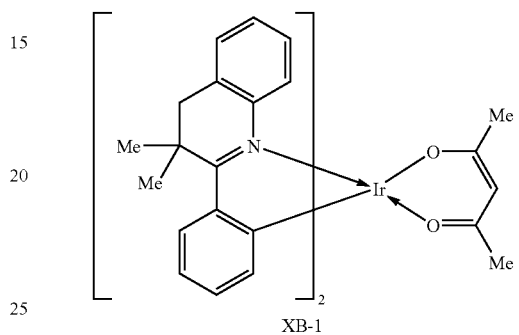
XB-1
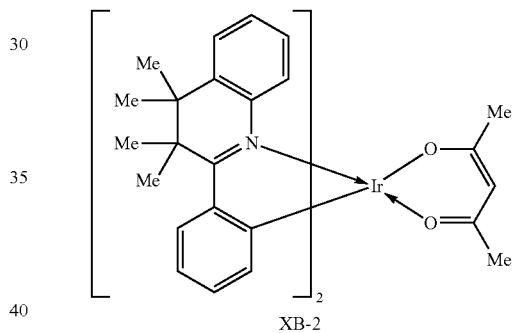
XB-2
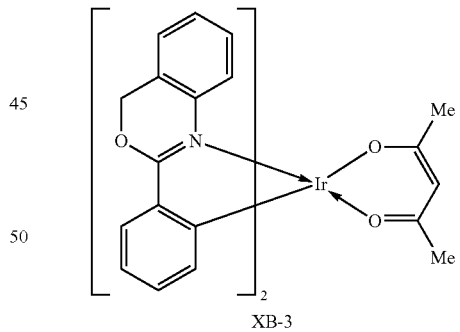
XB-3
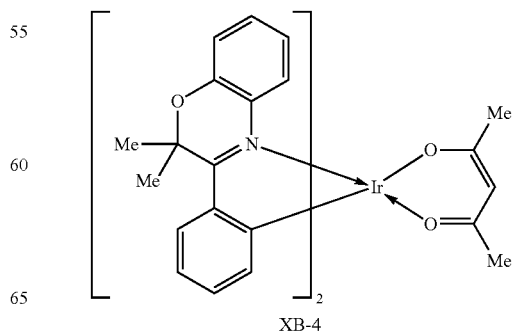
XB-4

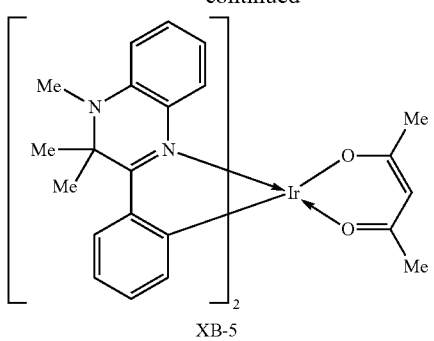
XB-5
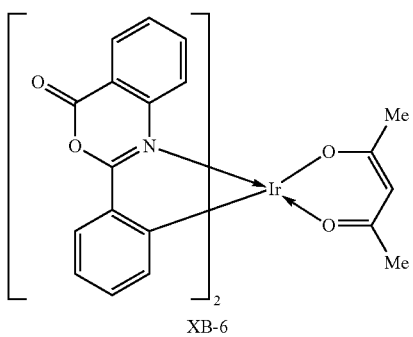
XB-6
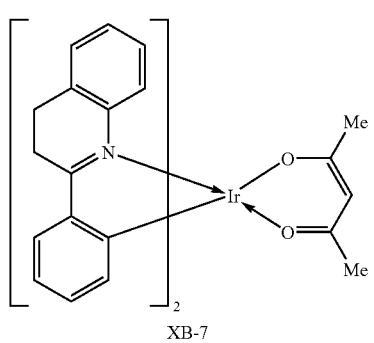
XB-7
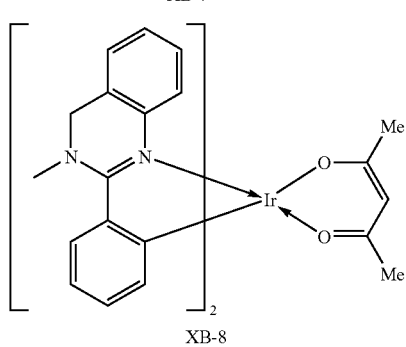
XB-8
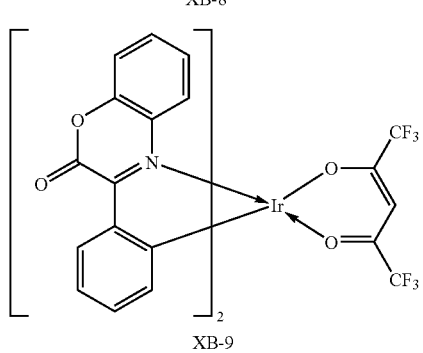
XB-9
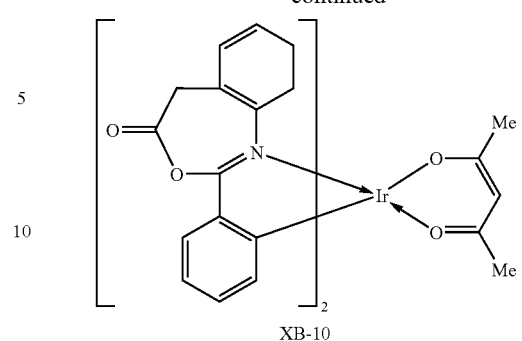
XB-10
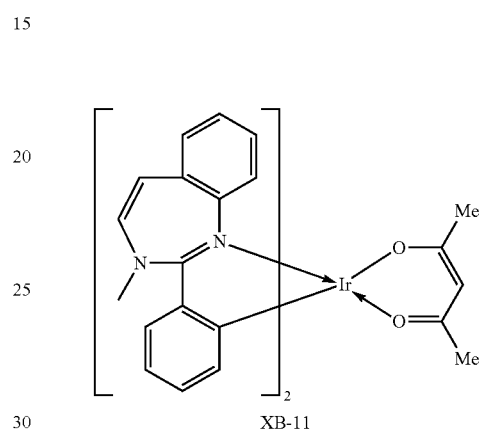
XB-11
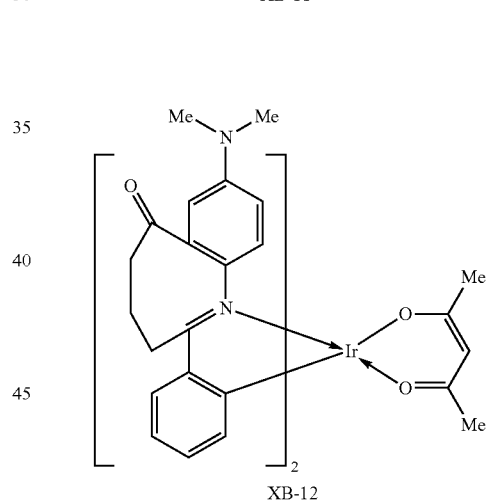
XB-12
General Formula (19)
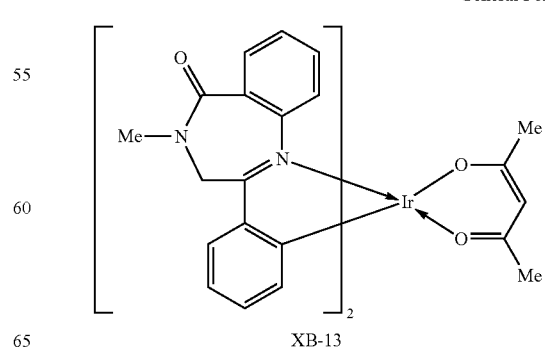
XB-13

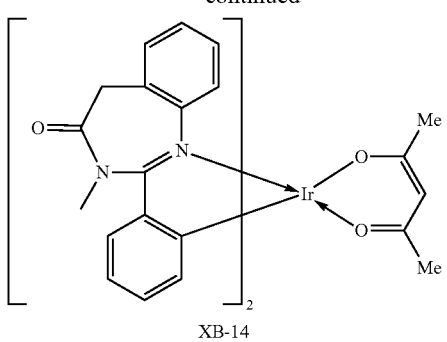
XB-14
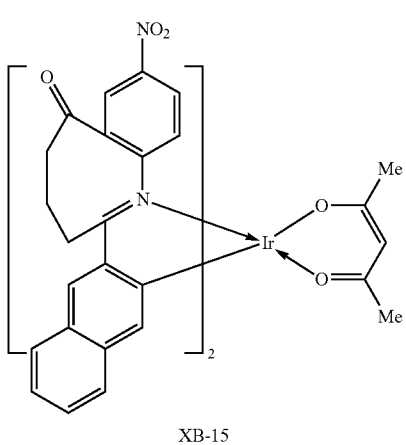
XB-15
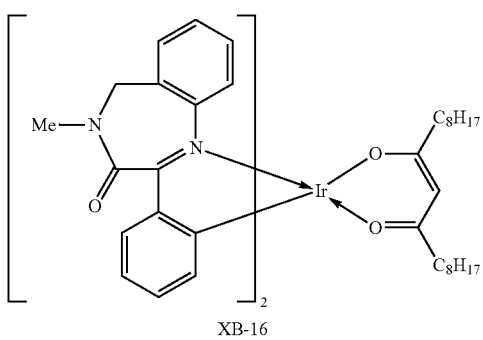
XB-16
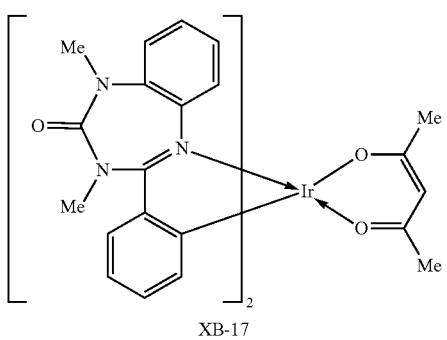
XB-17
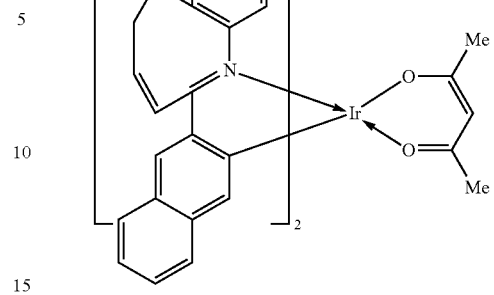
XB-18
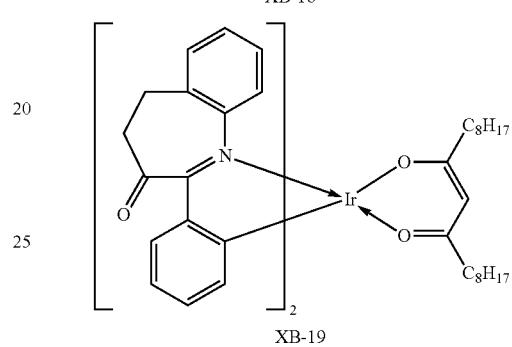
XB-19
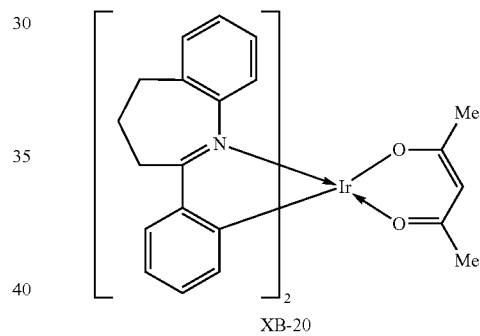
XB-20
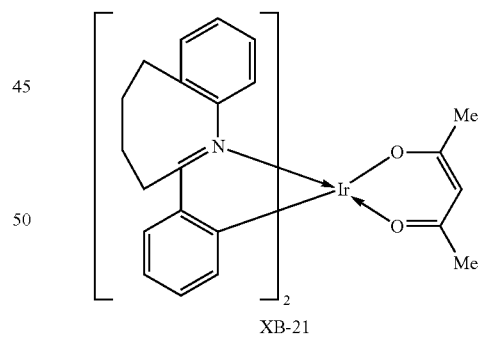
XB-21
General Formula (20)
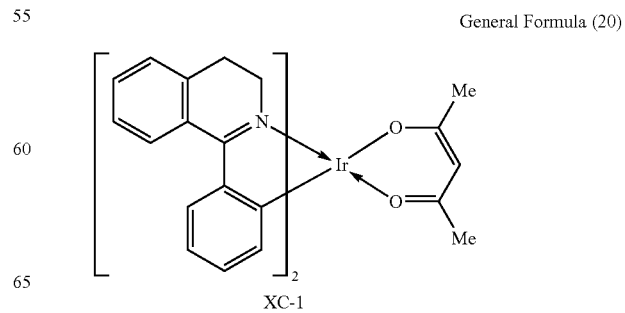
XC-1

-continued
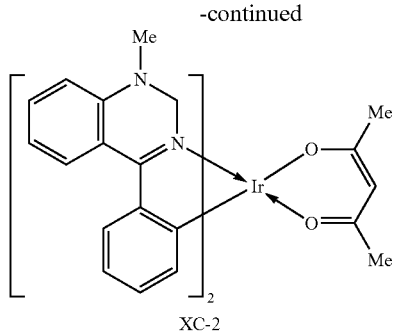
XC-2
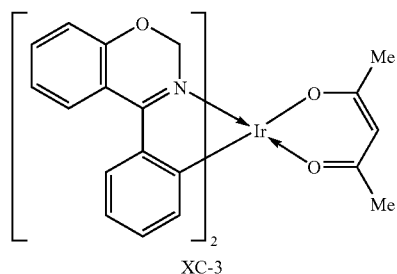
XC-3
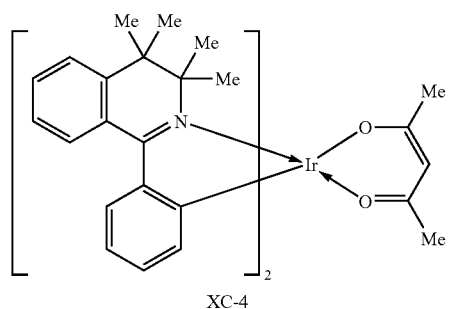
XC-4
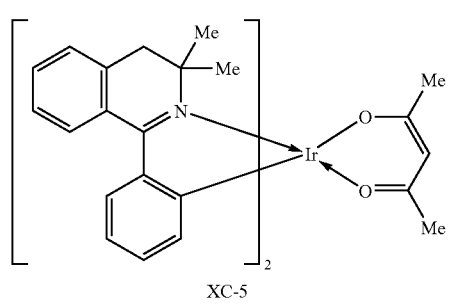
XC-5
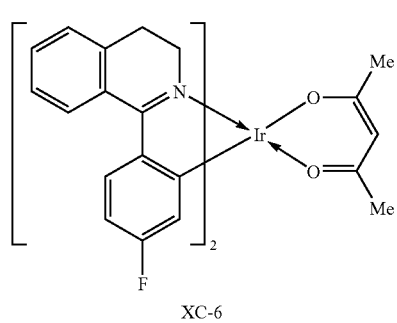
XC-6
-continued
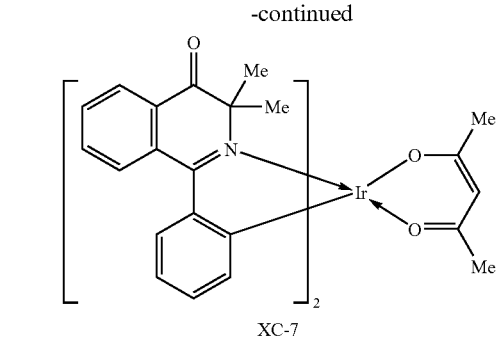
XC-7
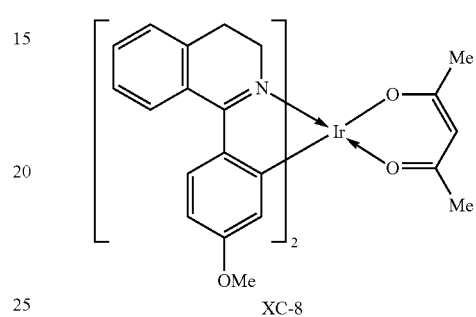
XC-8
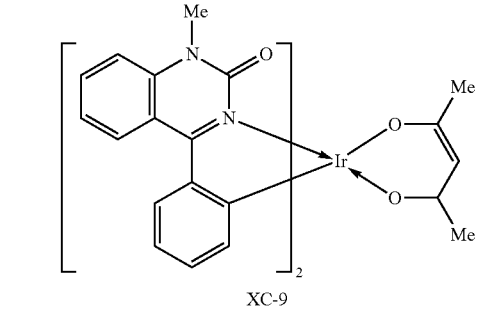
XC-9
General Formula (21)
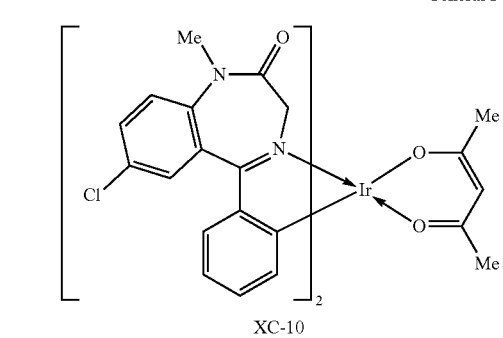
XC-10
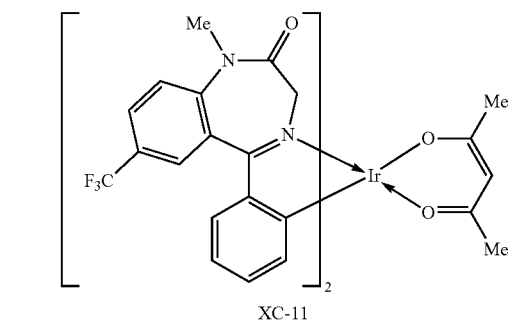
XC-11

-continued
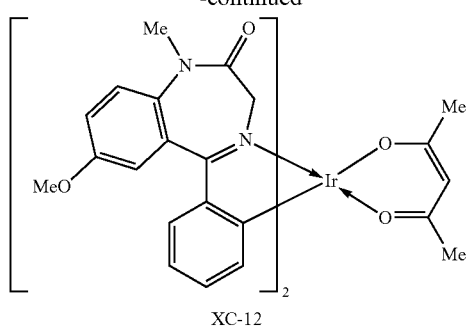
XC-12
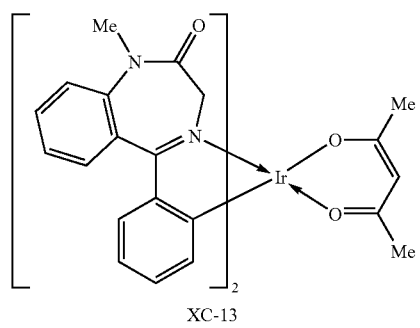
XC-13
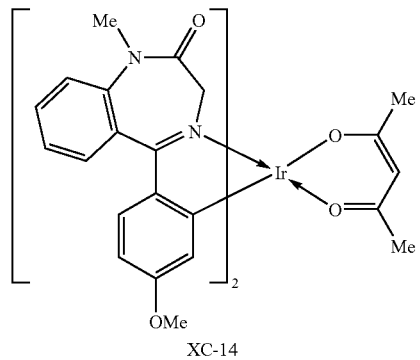
XC-14
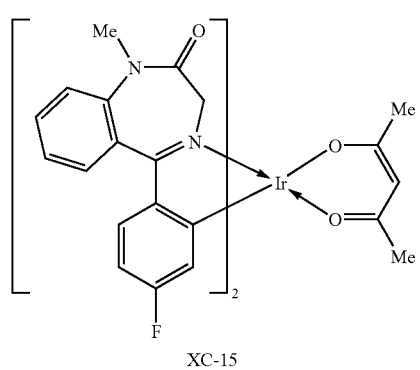
XC-15
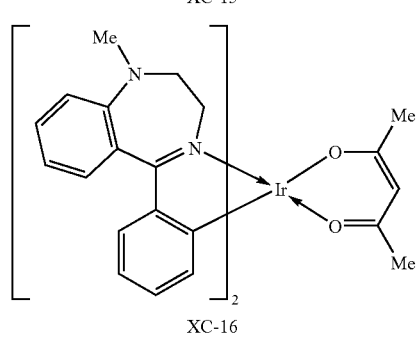
XC-16
-continued
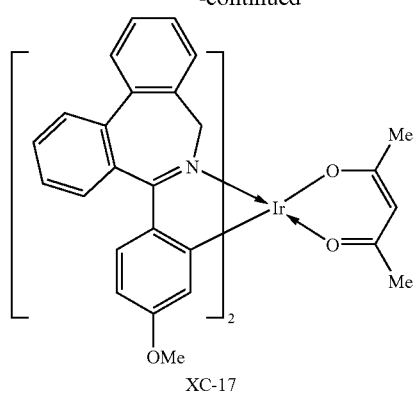
XC-17
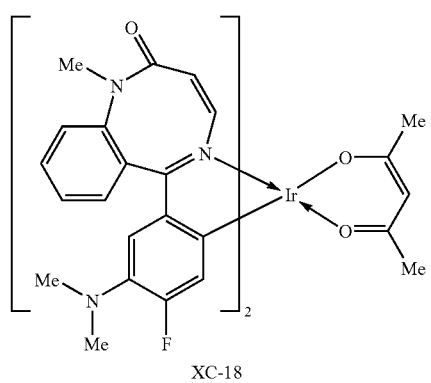
XC-18
General Formula (22)
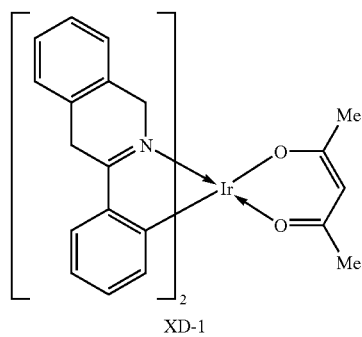
XD-1
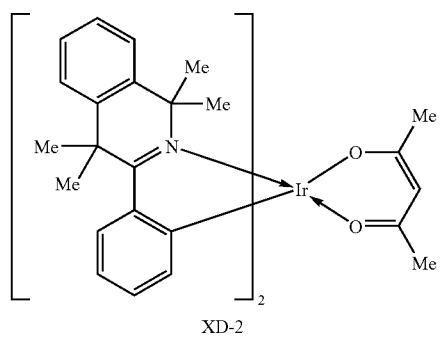
XD-2

-continued
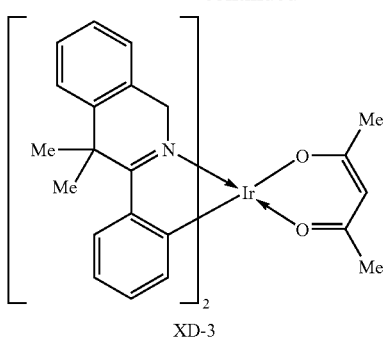
XD-3
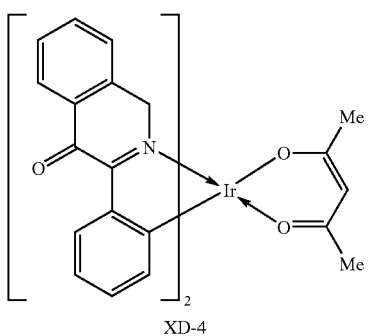
XD-4
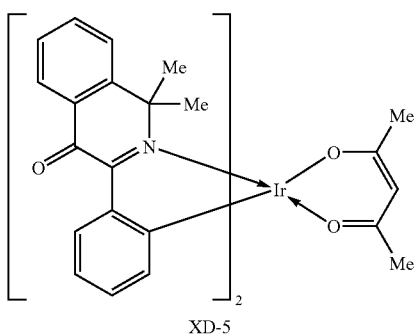
XD-5
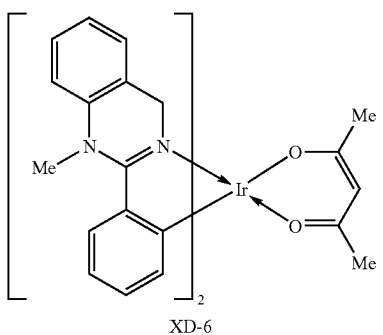
XD-6
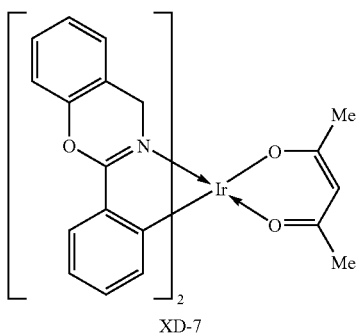
XD-7
-continued
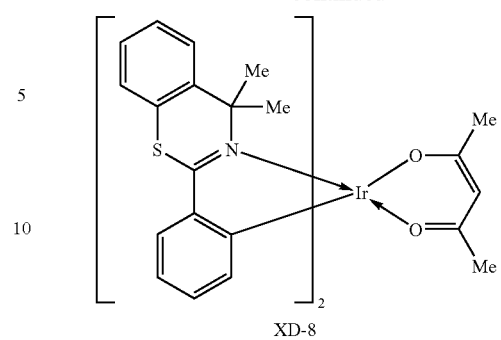
XD-8
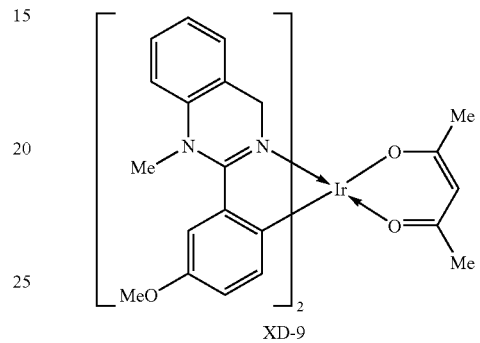
XD-9
General Formula (23)
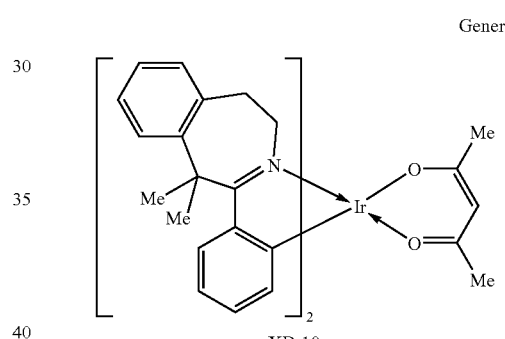
XD-10
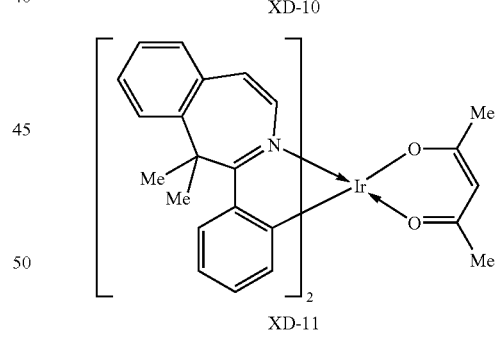
XD-11
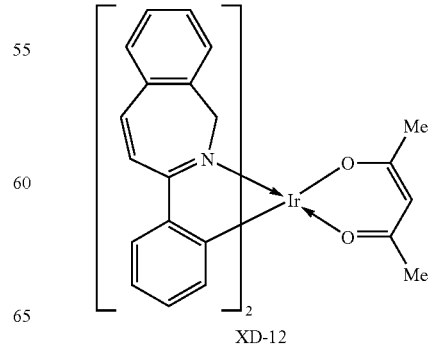
XD-12

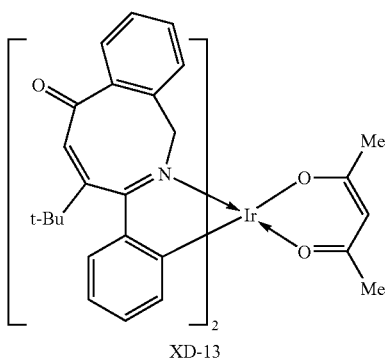
XD-13
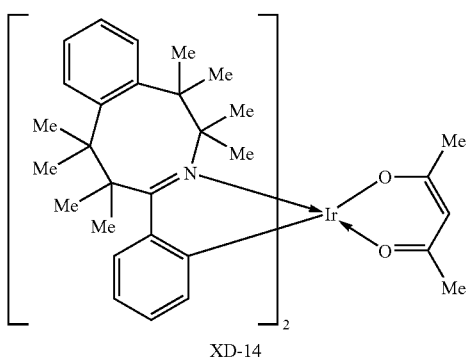
XD-14
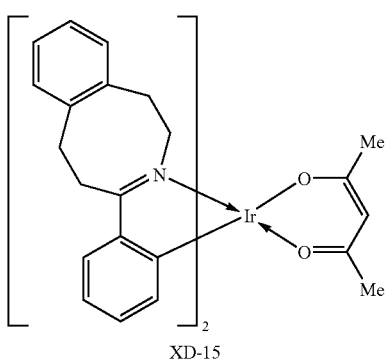
XD-15
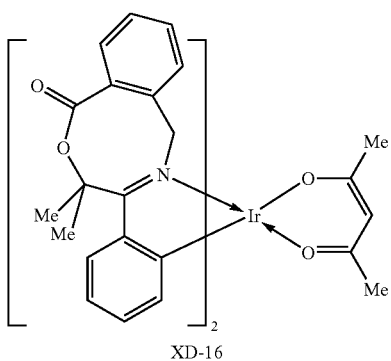
XD-16
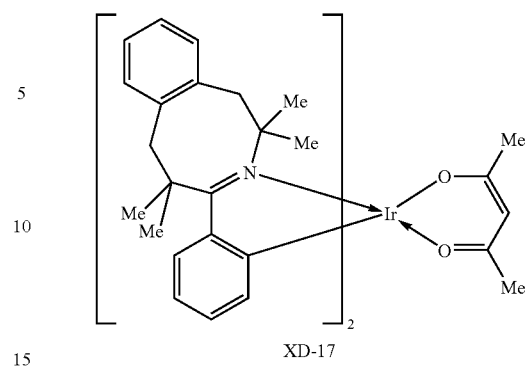
XD-17
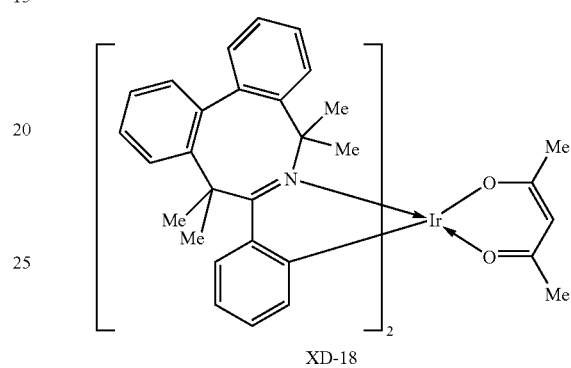
XD-18
General Formula (24)
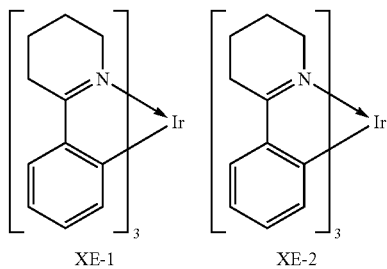
XE-1  XE-2
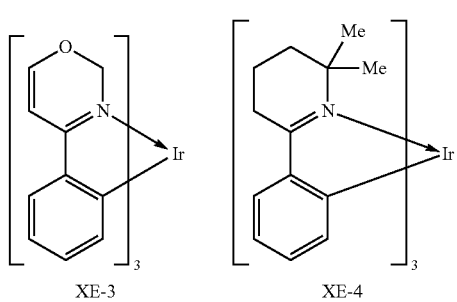
XE-3  XE-4
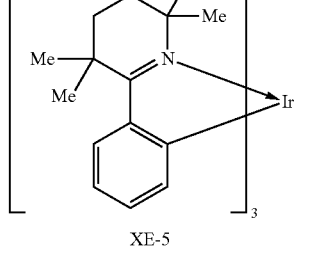
XE-5

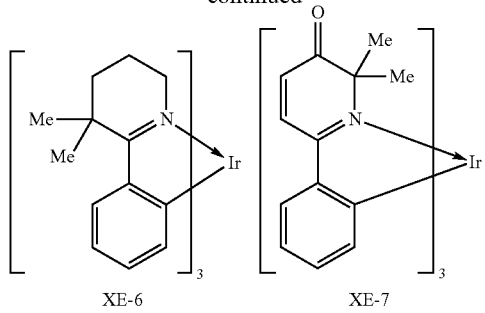
XE-6 XE-7
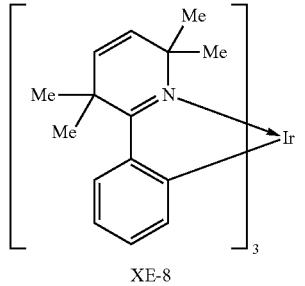
XE-8
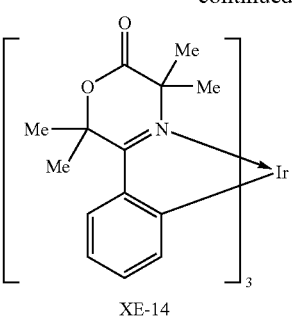
XE-14
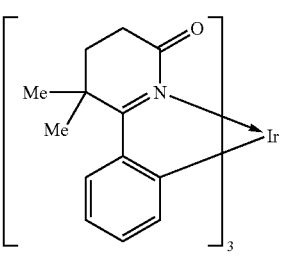
XE-15
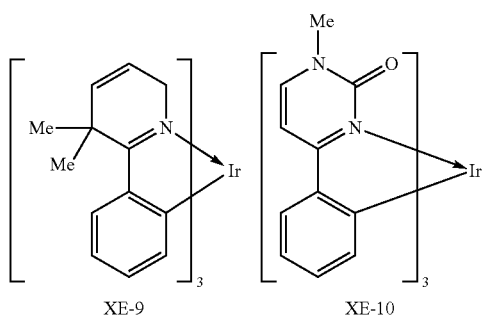
XE-9 XE-10
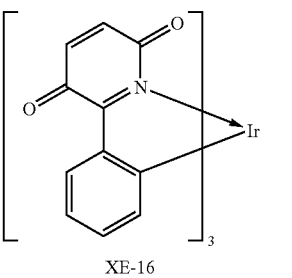
XE-16
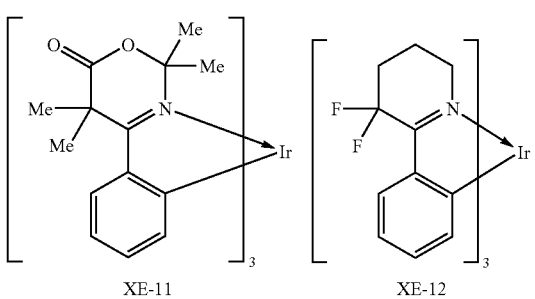
XE-11 XE-12
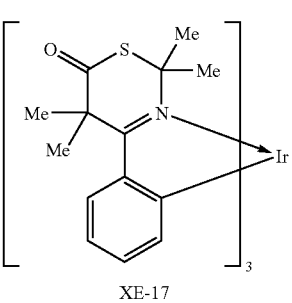
XE-17
General Formula (25)
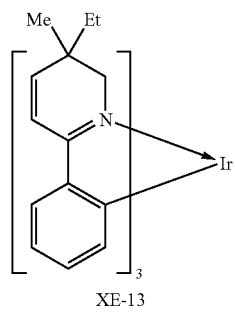
XE-13
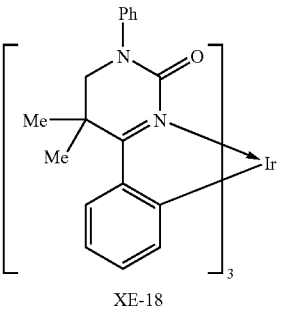
XE-18

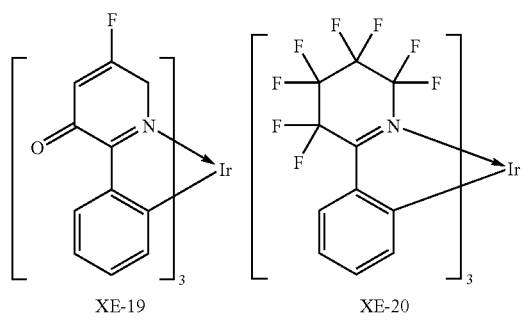
XE-19    XE-20
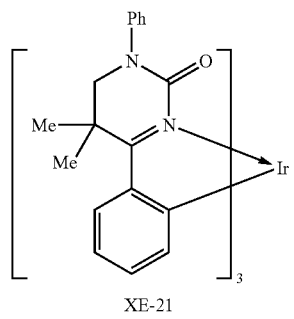
XE-21
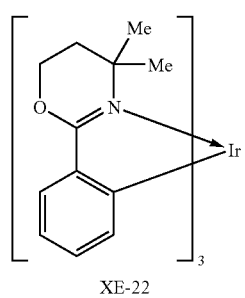
XE-22
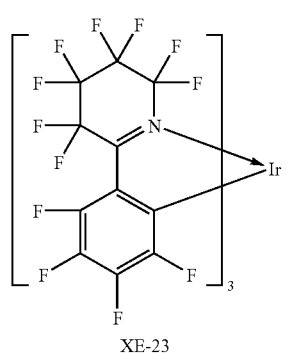
XE-23
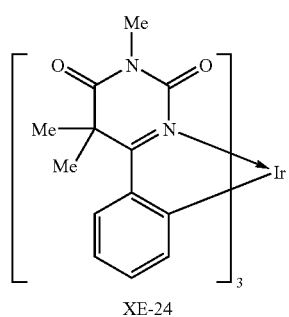
XE-24
General Formula (26)
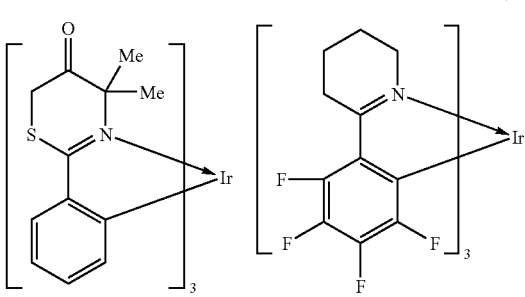
XE-25    XE-26
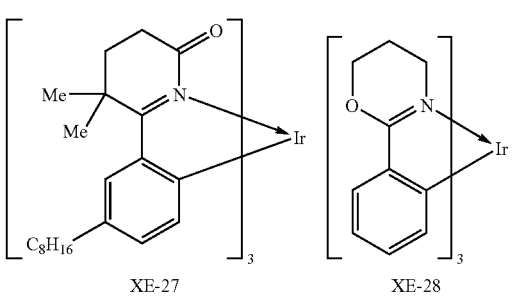
XE-27    XE-28
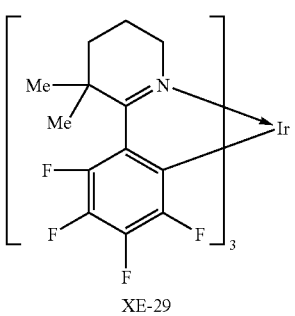
XE-29
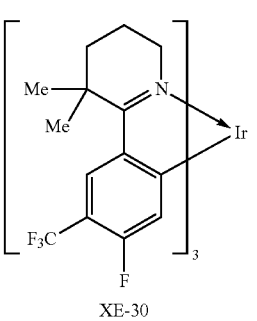
XE-30
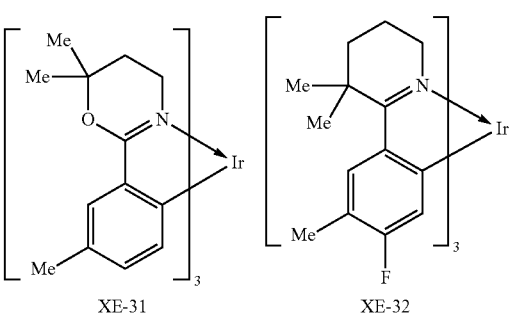
XE-31    XE-32

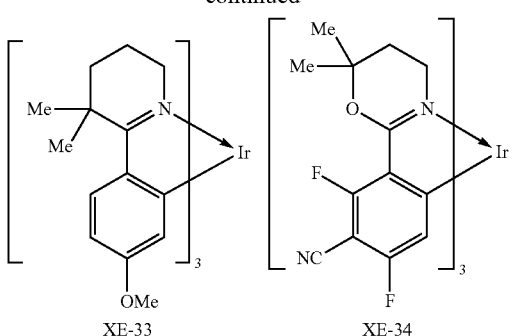
XE-33  XE-34
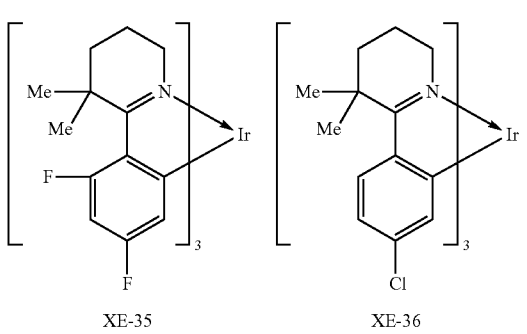
XE-35  XE-36
General Formula (27)
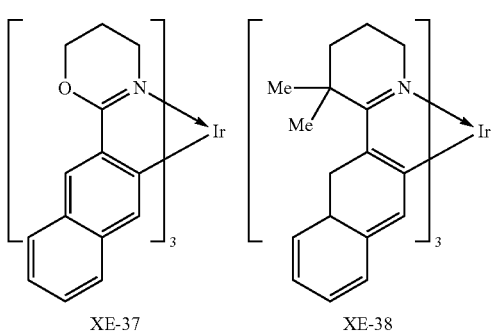
XE-37  XE-38
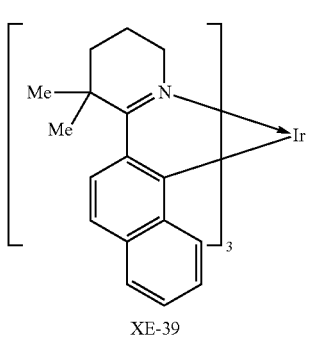
XE-39
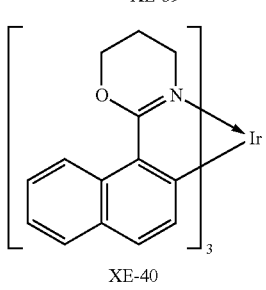
XE-40
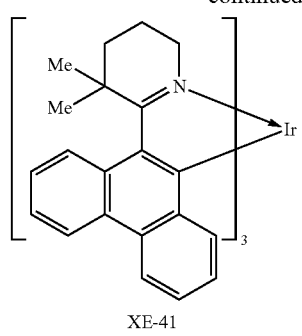
XE-41
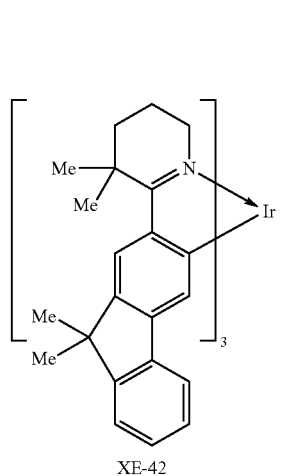
XE-42
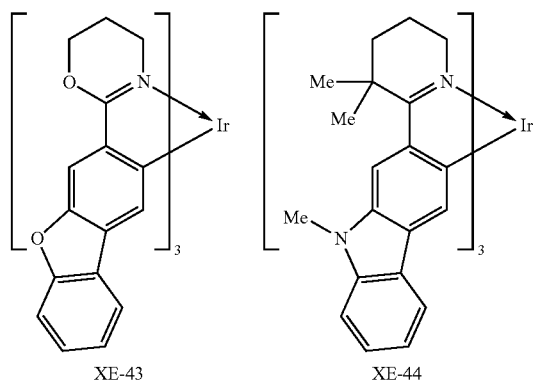
XE-43  XE-44
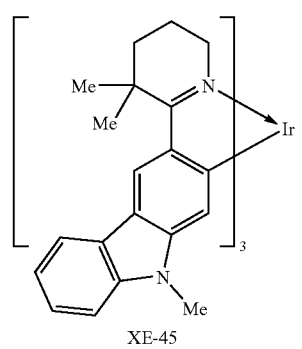
XE-45

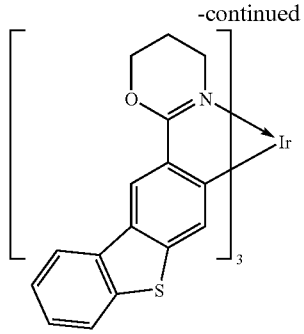
XE-46
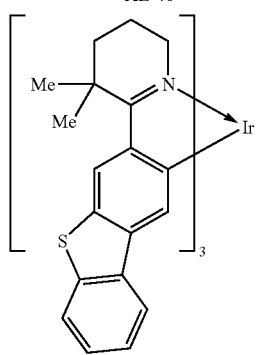
XE-47
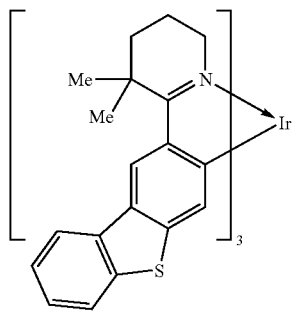
XE-48
General Formula (28)
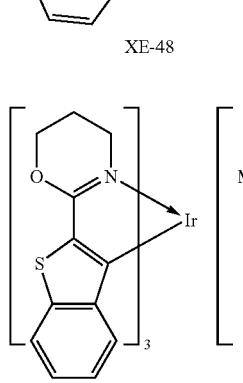
XE-49
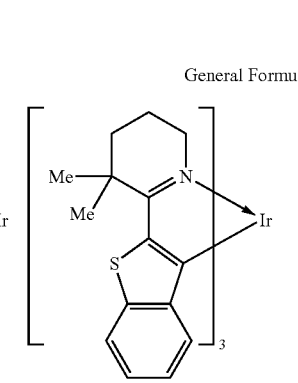
XE-50
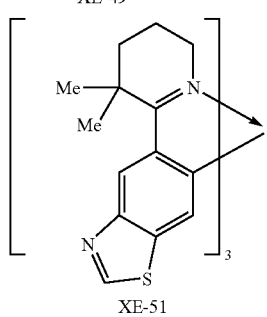
XE-51
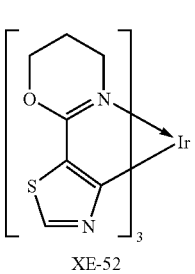
XE-52
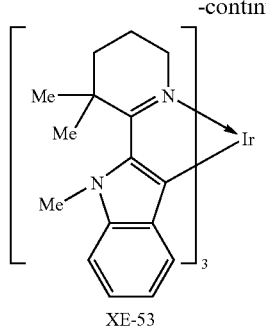
XE-53
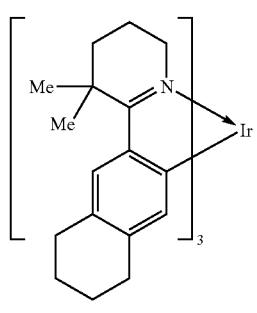
XE-54
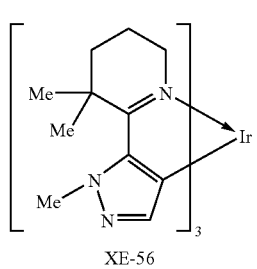
XE-55
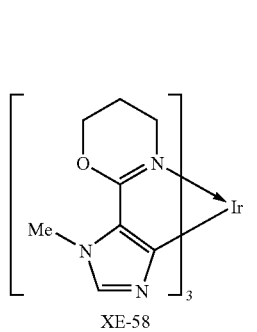
XE-56
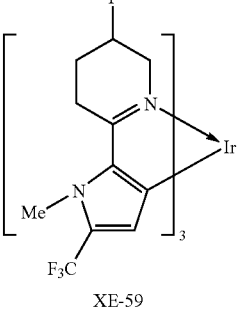
XE-57
General Formula (29)
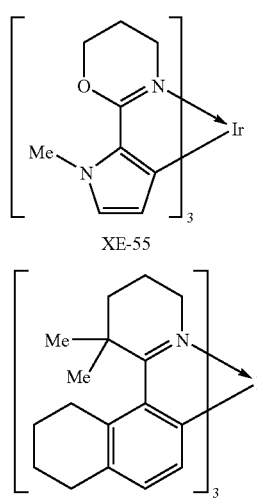
XE-58
XE-59
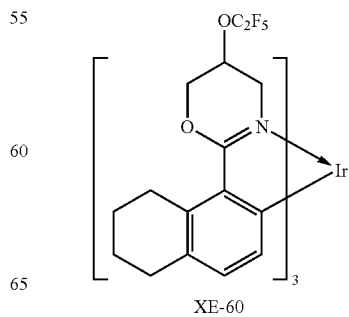
XE-60

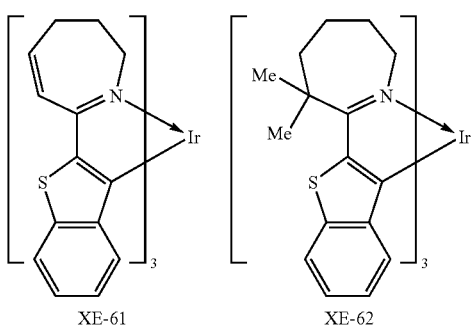
XE-61　　XE-62
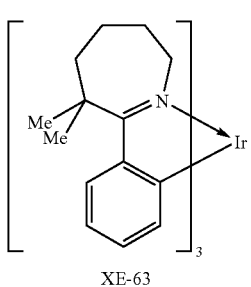
XE-63
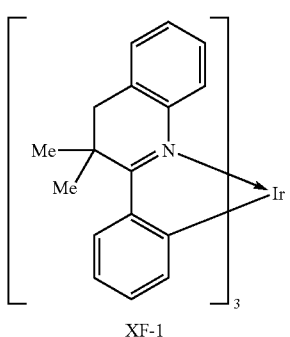
XF-1
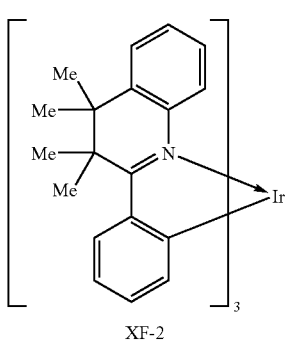
XF-2
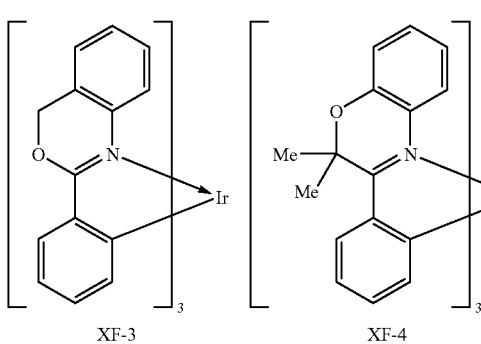
XF-3　　XF-4
General Formula (30)
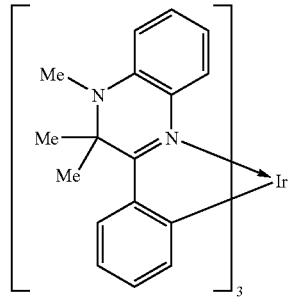
XF-5
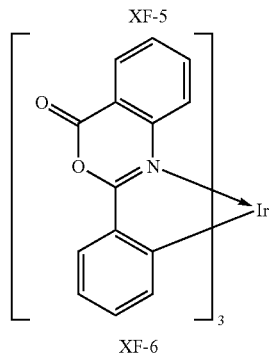
XF-6
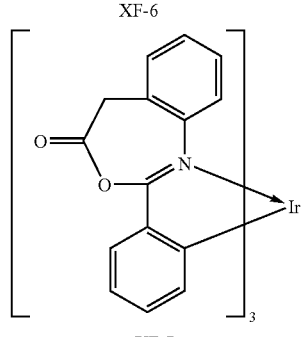
XF-7
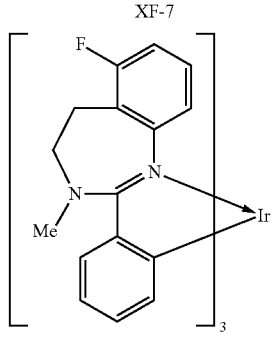
XF-8
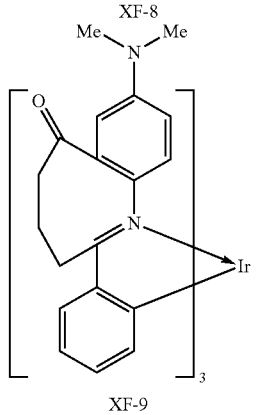
XF-9

General Formula (31)
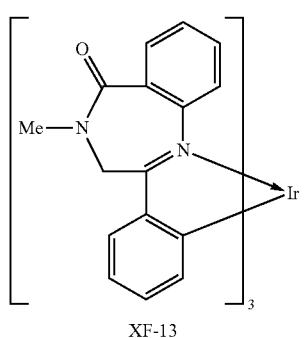
XF-13
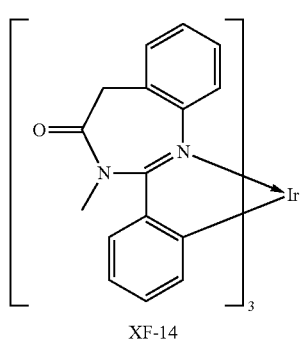
XF-14
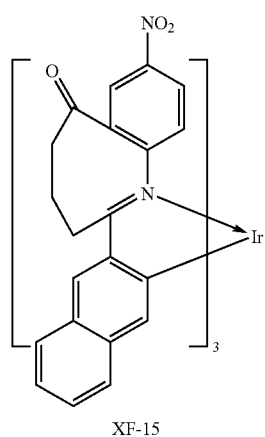
XF-15
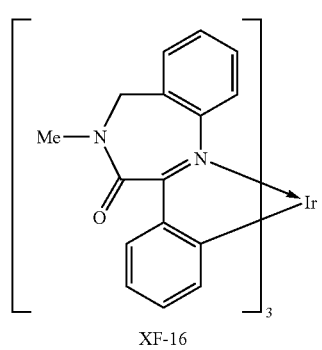
XF-16
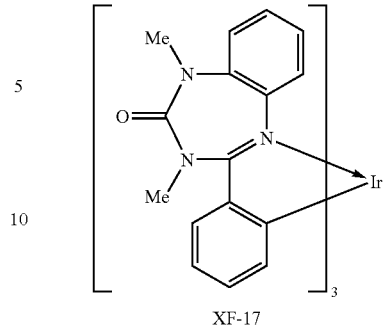
XF-17
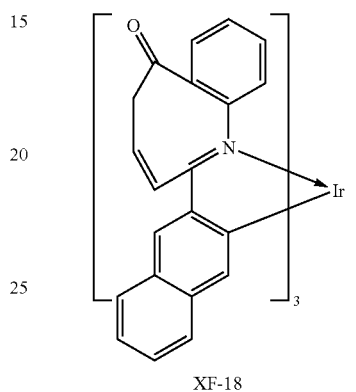
XF-18
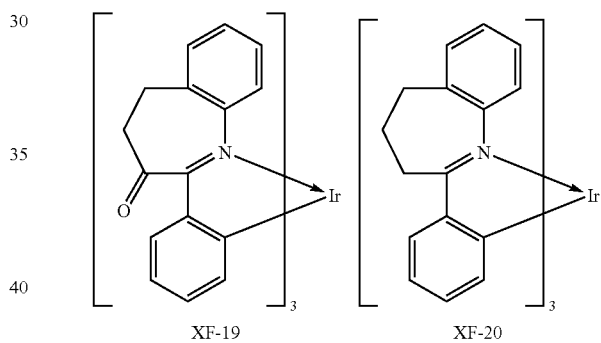
XF-19    XF-20
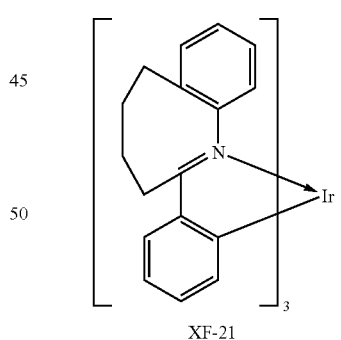
XF-21
General Formula (32)
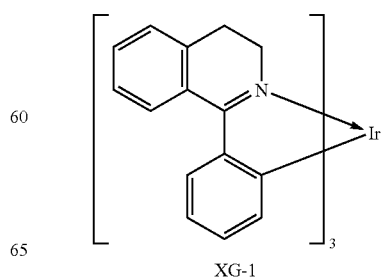
XG-1

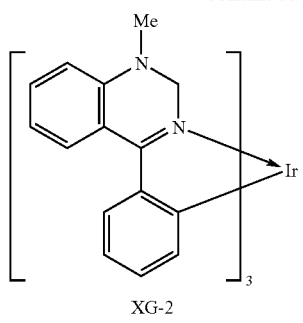
XG-2
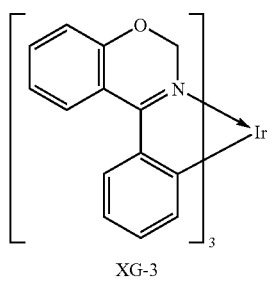
XG-3
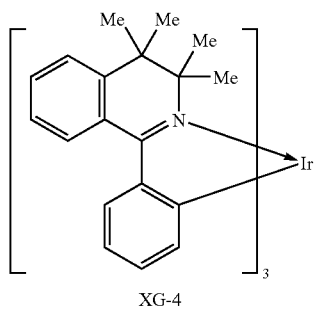
XG-4
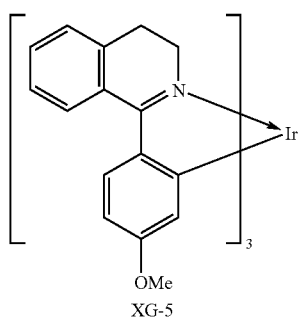
XG-5
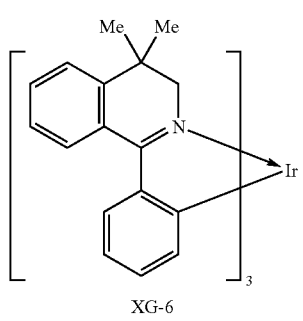
XG-6
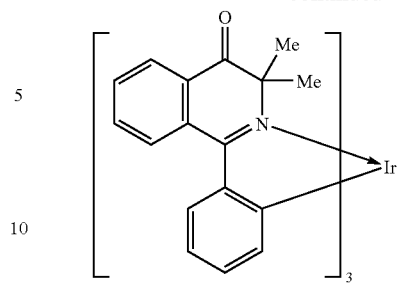
XG-7
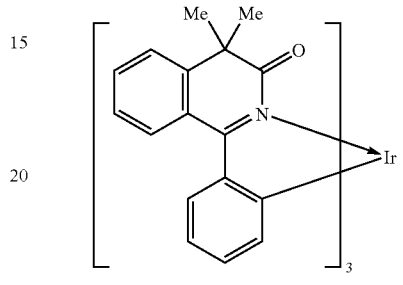
XG-8
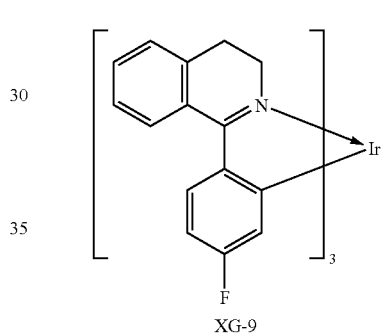
XG-9
General Formula (33)
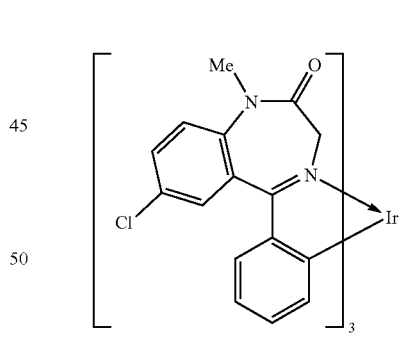
XG-10
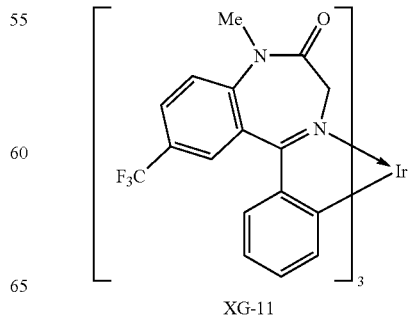
XG-11

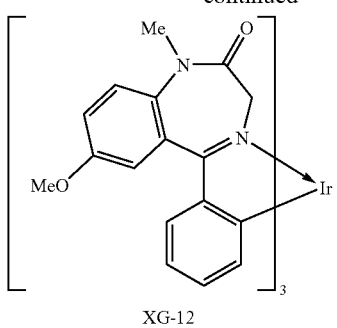
XG-12
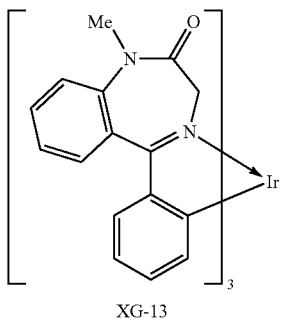
XG-13
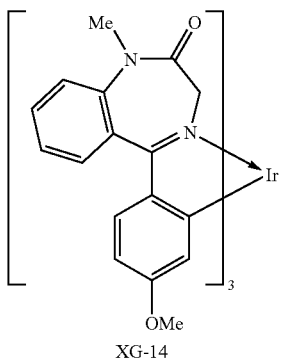
XG-14
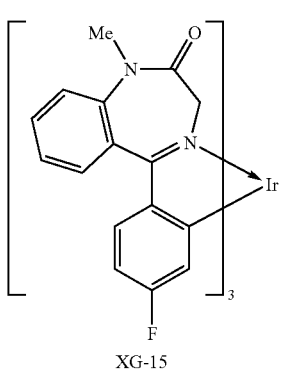
XG-15
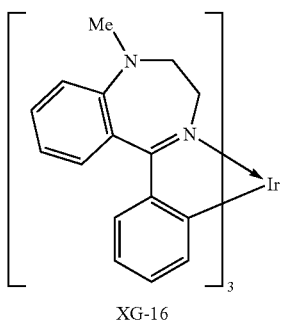
XG-16
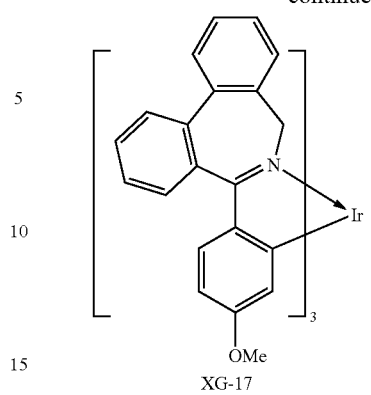
XG-17
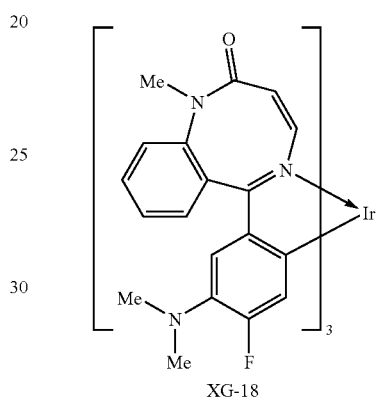
XG-18
General Formula (34)
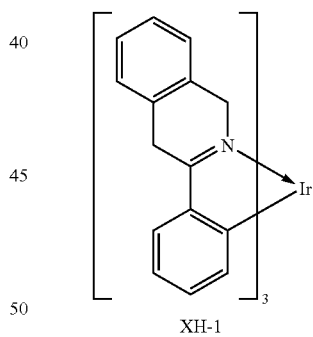
XH-1
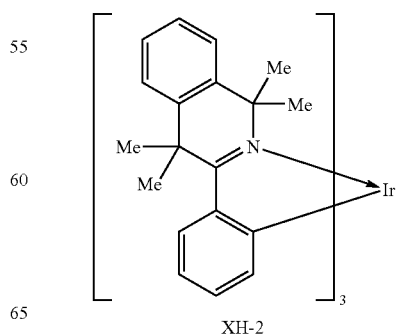
XH-2

-continued
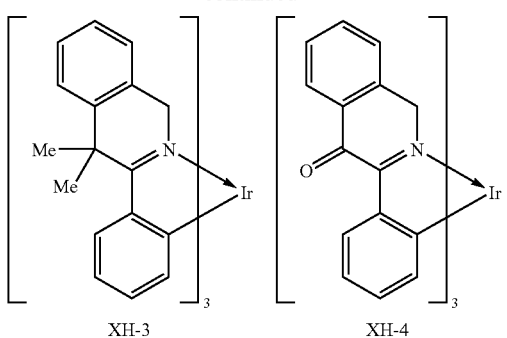
XH-3  XH-4
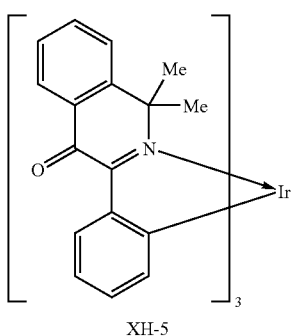
XH-5
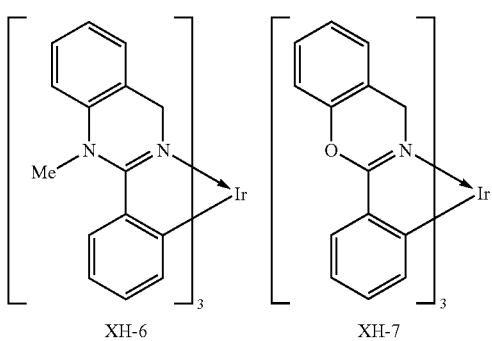
XH-6  XH-7
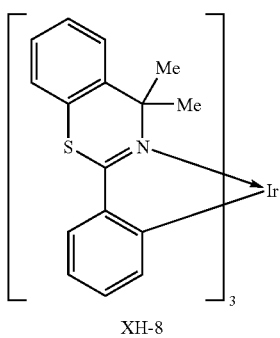
XH-8
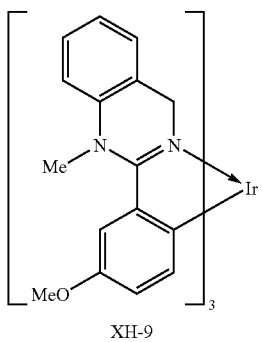
XH-9
-continued
General Formula (35)
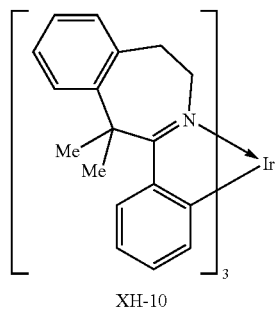
XH-10
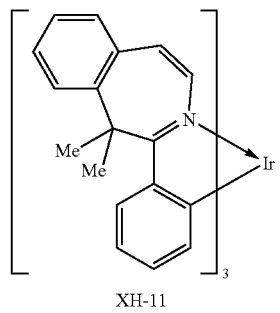
XH-11
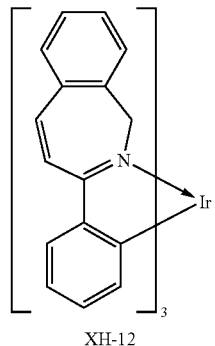
XH-12
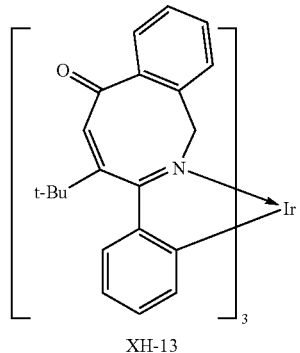
XH-13
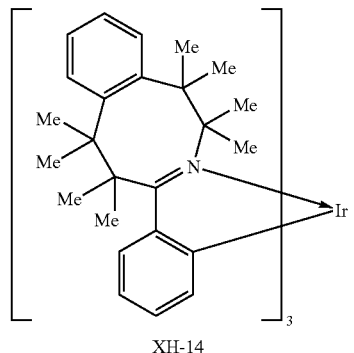
XH-14

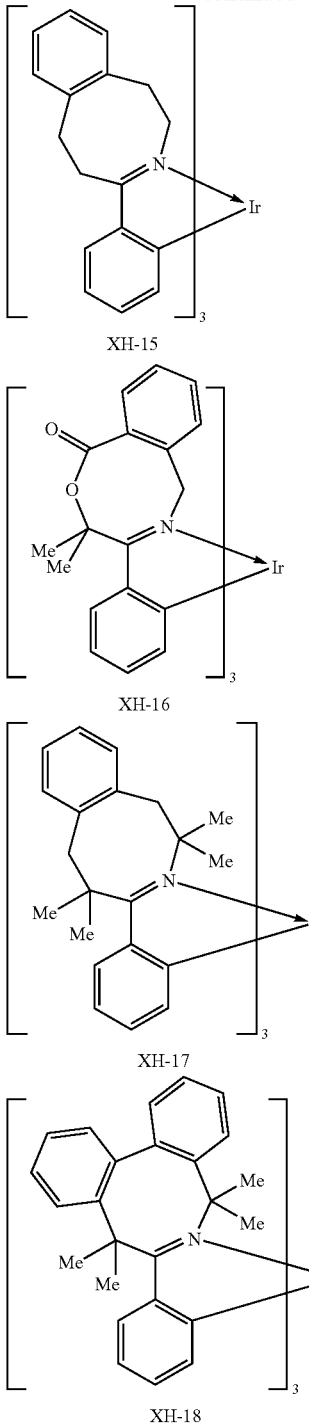

XH-15

XH-16

XH-17

XH-18

Next, a light-emitting device of the present invention will be described.

An organic layer containing the metal complex of the present invention can be prepared by any one of film formation methods such as a vacuum evaporation method, a casting method, a coating method, and a spin coating method, and the inkjet method.

Figure 2:
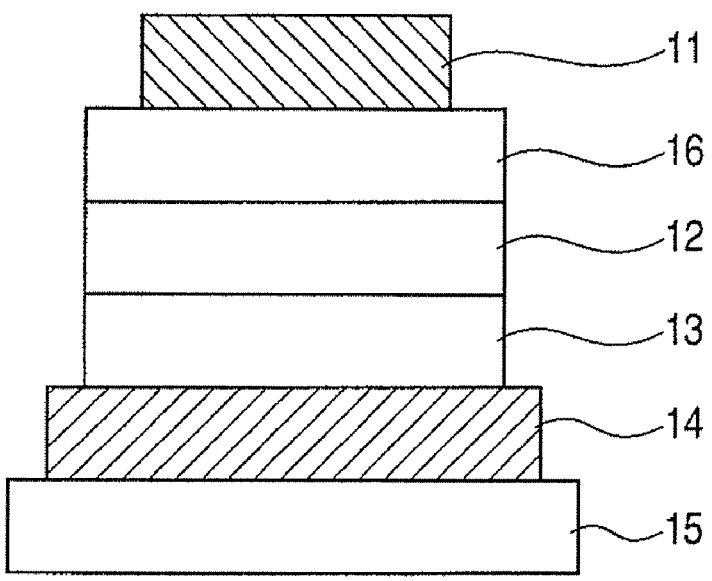
FIG. 2 shows another example of the organic EL device of the present invention.
Figure 3:
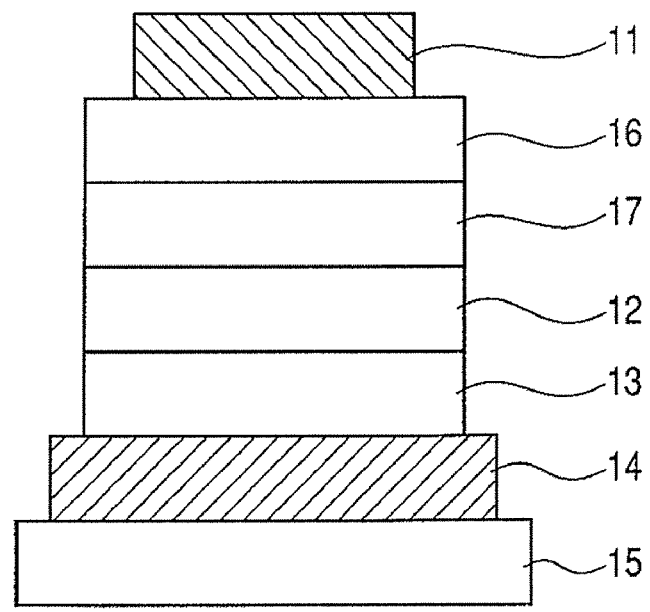
FIG. 3 shows another example of the organic EL device of the present invention.

FIGS. 1 to 3 show basic device structures of the light-emitting device of the present invention.

First, reference characters shown in the drawings are described as follows: 11 denotes a metal electrode; 12 denotes a light-emitting layer; 13 denotes a hole-transporting layer; 14 denotes a transparent electrode; 15 denotes a transparent substrate; 16 denotes an electron-transporting layer; and 17 denotes an exciton diffusion-prevention layer.

As shown in FIGS. 1 to 3, an organic EL device generally includes: a transparent substrate 15; a transparent electrode 14 having a thickness of 50 to 200 nm, which is arranged on the transparent substrate; multiple organic layers; and a metal electrode 11, where the multiple organic layers is interposed between the transparent electrode and the metal electrode.

FIG. 1 shows an example in which the organic film layers include a light-emitting layer 12 and a hole-transporting layer 13. ITO having a large work function is used for the transparent electrode 14 to facilitate the injection of a hole from the transparent electrode 14 to the hole-transporting layer 13. A metal material having a small work function such as aluminum, magnesium, or an alloy thereof is used for the metal electrode 11 to facilitate the injection of electrons to the organic layers.

The metal complex of the present invention is used for the light-emitting layer 12. A material having electron-donating properties such as a triphenyldiamine derivative typified by α-NPD shown below can be appropriately used for the hole-transporting layer 13.

General Formula (36)

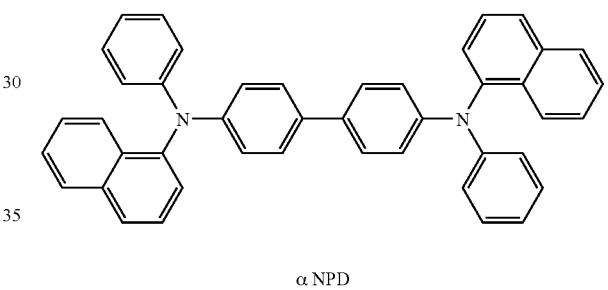

α NPD

The device having the above-mentioned constitution exhibits rectifying property. When an electric field is applied in such a manner that the metal electrode 11 serves as a cathode and the transparent electrode 14 serves as an anode, electrons are injected from the metal electrode 11 into the light-emitting layer 12 and holes are injected from the transparent electrode 14.

The injected holes and electrons are recombined in the light-emitting layer 12 to generate excitons, thereby emitting light. In this case, the hole-transporting layer 13 serves as an electron-blocking layer, and the recombination efficiency at the interface between the light-emitting layer 12 and the hole-transporting layer 13 increases, whereby the light emission efficiency increases.

In FIG. 2, an electron-transporting layer 16 is interposed between the metal electrode 11 and the light-emitting layer 12 shown in FIG. 1. In this case, the light emission efficiency is increased by separating a light emitting function and electron- and hole-transporting functions to provide a carrier blocking structure having improved effectiveness. An oxadiazole derivative can be used for the electron-transporting layer 16.

As shown in FIG. 3, it is also preferable to adopt a four-layer structure composed of, from the side of the transparent electrode 14 serving as an anode, the hole-transporting layer 13, the light-emitting layer 12, an exciton diffusion-prevention layer 17, the electron-transporting layer 16, and the metal electrode 11.

Such a light-emitting device high in efficiency as shown in the present invention can be applied to products which require energy saving or high luminance. Examples of applications include a light source for a display apparatus, an illumination apparatus and a printer, and a backlight for a liquid crystal display apparatus. The application of the light-emitting device of the present invention to a display apparatus can provide an organic light-emitting device having a unit for supplying an electric signal, and specifically, a lightweight and energy-saving flat panel display with high visibility. In addition, as for the light source of a printer, the light-emitting device of the present invention can be substituted for a laser light source for a laser beam printer which is widely used at present. Independently addressable devices are arranged in an array, and a photosensitive drum is exposed to light in a desired manner to form images. The use of the light-emitting device of the present invention can significantly reduce the volume of an apparatus. The light-emitting device of the present invention is expected to provide an energy-saving effect on the illumination apparatus or the backlight.

The light-emitting device of the present invention may be applied to a display in such a manner that it is driven using an active-matrix TFT drive circuit.

Figure 4:
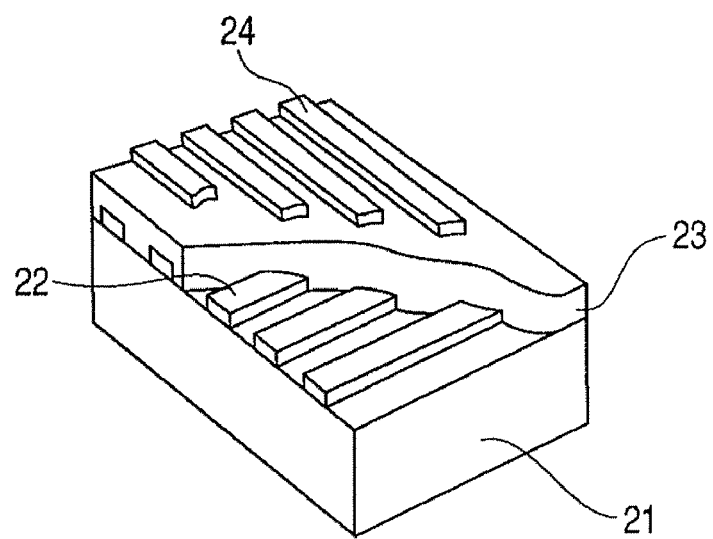
FIG. 4 is a schematic view of a passive type of organic EL device.
Figure 5:
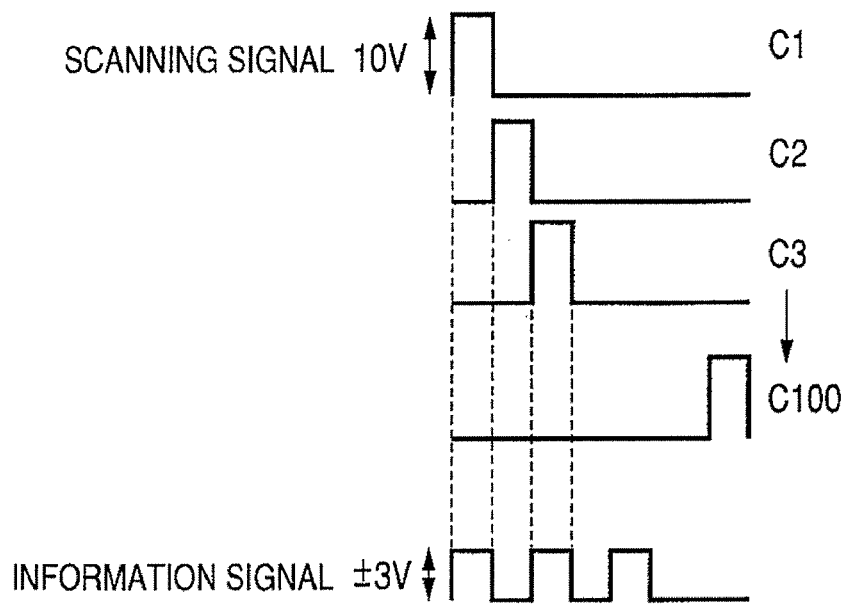
FIG. 5 shows a pixel circuit of a panel.

In the following, an example in which an active-matrix substrate is used in the device of the present invention is described with reference to FIGS. 4 to 6. FIG. 4 schematically illustrates an example of a passive type of EL device. In FIG. 4, 21 denotes a glass substrate; 22, an ITO electrode; 23, an organic compound layer; and 24, a cathode. The panel is equipped with a scanning signal driver, an information signal driver, and a current supply source, which are connected to gate selection lines, information signal lines and current supply lines, respectively. A pixel circuit shown in FIG. 5 is arranged on an intersection of the gate selection line and the information signal line. The scanning signal driver sequentially selects the gate selection lines G1, G2, G3, . . . Gn, and image signals are applied to the gate selection lines from the information signal driver in synchronization therewith.

Next, the operation of the pixel circuit will be described. In the pixel circuit, when a selected signal is applied to the gate selection line, TFT 1 is turned on to supply an image signal to Cadd so that a gate potential of TFT 2 is determined. An electric current is supplied to the organic EL device from the current supply line according to the gate potential of TFT 2. Since the gate potential of TFT 2 is retained at the potential of Cadd until TFT 1 is again scanned and selected, the gate potential of TFT 2 continues to flow in the EL device until the next scanning is performed. Thus, it is possible to emit light constantly during a one frame period of time.

Figure 6:
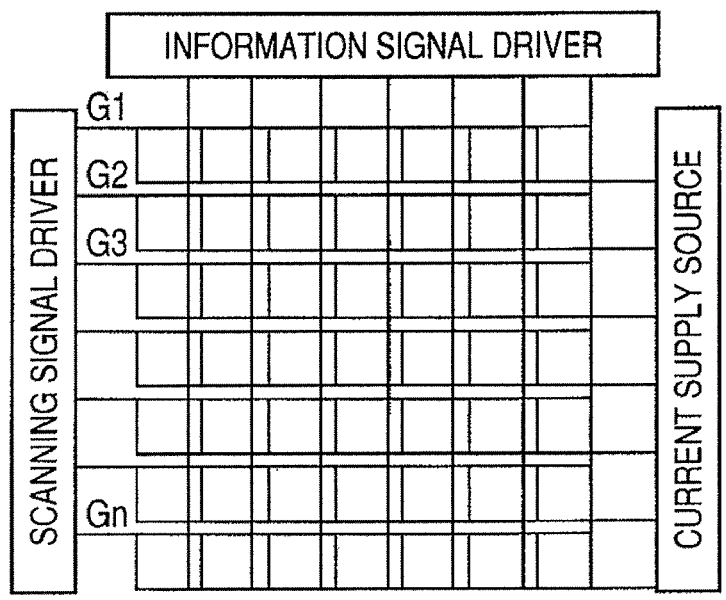
FIG. 6 is a schematic view illustrating an example of a TFT substrate to be used in the present invention.

FIG. 6 schematically illustrates an example of a TFT substrate to be used in the present invention, in which a p-Si layer is arranged on a glass substrate, and necessary impurities are doped in channel, drain and source regions, respectively. On the regions, a gate electrode is formed through a gate-insulating film, and a drain electrode and a source electrode are so formed as to be connected to the drain region and the source region, respectively. An insulating layer and an ITO electrode as a pixel electrode are superposed thereon, and the ITO electrode and the drain electrode are connected through a contact hole.

In the present invention, a switching device is not particularly limited, and a single-crystal silicon substrate, an MIM device or an a-Si type device can easily be adopted.

An organic EL display panel can be obtained by sequentially superposing a multi-layered or single-layered organic EL layer/anode layer on the ITO electrode. The display panel using the organic compound of the present invention can be driven to constantly display images with good image quality for a long period of time.

In the present invention, a unit for supplying electric signals includes at least the switching device.

EXAMPLES

Hereinafter, the present invention will be described specifically by way of examples. However, the present invention is not limited to these examples.

Synthesis methods necessary for synthesizing the novel metal coordination compounds of the present invention are described in detail by referring to typical synthesis examples.

A ligand can be synthesized by a synthesis method described in any one of the following articles.

Tetrahedron Lett., 40, 3701, (1999).; J. Am. Chem. Soc., 59, 984 (1937); Tetrahedron Lett., 34, 6205, (1993); J. Fluorine Chem., 52, 389 (1991); Syn. Lett., 47 (1998); J. Am. Chem. Soc., 126, 13244 (2004); J. Org. Chem., 49, 4397 (1984).; J. Heterocycl. Chem., 523 (1990); Tetrahedron, 39, 3373 (1983); J. Heterocycl. Chem., 1457 (1980); J. Chem. Soc., 1343 (1951); J. Org. Chem., 51, 4147 (1986); J. Org. Chem., 45, 1675 (1980); J. Am. Chem. Soc., 112, 3969 (1990); J. Heterocycl. Chem., 615 (1970); J. Org. Chem., 43, 3817 (1978).

Example 1

(Synthesis of Compound XX-1)

7.06 g (20 mmol) of iridium (III) chloride, 8.28 g (40 mmol) of Compound XL-1, and 100 ml of ethoxyethanol were fed into a 300-ml three-necked flask, and stirred at room temperature for 30 minutes in a stream of nitrogen, followed by stirring at 80° C. for 8 hours. After that, a reaction product was allowed to cool to room temperature, and a precipitate was filtrated off, and washed sequentially with water, ethanol, and acetone. The resultant product was dried under reduced pressure at room temperature to yield 5.9 g (68% yield) of Compound XX-1.

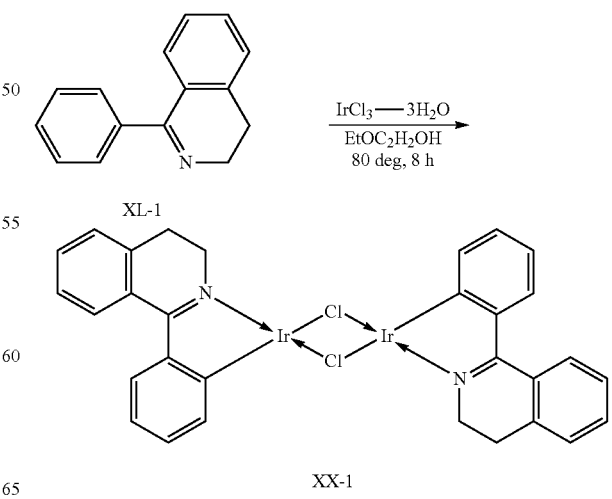

General Formula (37)

Example 2

(Synthesis of Exemplary Compound XC-1)

100 ml of ethoxyethanol, 5.9 g (6.79 mole) of Compound XX-1, 2.4 g (20 mmol) of acetylacetone, and 3.6 g (34 mmol) of sodium carbonate were fed into a 300-ml three-necked flask and stirred at room temperature in a stream of nitrogen, followed by stirring at 80° C. for 8 hours. After that, a reaction product was allowed to cool to room temperature, and a precipitate was filtrated off and washed with water to yield 3.9 g (40% yield) of Exemplary Compound XC-1.

$^1$H NMR (CDCl$_3$, 500 MHz) σ(ppm): 8.01 (m, 2H), 7.73 (m, 2H) 7.45 (m, 4H), 7.40 (m, 2H), 6.92 (m, 2H), 6.81 (m, 2H), 6.76 (m, 2H), 5.21 (s, 1H), 4.15 (m, 2H), 3.86 (m, 2H), 3.10 (m, 2H), 2.91 (m, 2H), 1.79 (s, 6H).

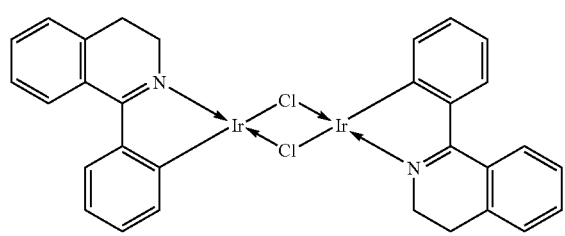

XX 1

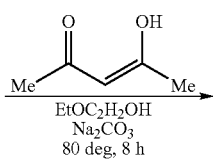

General Formula (38)

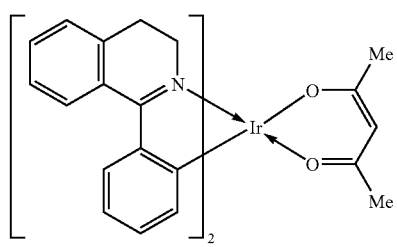

XC-1

Example 3

(Synthesis of Exemplary Compound XG-1)

1 g (1.42 mmol) of Exemplary Compound XC-1 and 10 g (48 mmol) of Compound XL-1 were fed into a 50-ml two-necked flask, and heated and stirred at around 160° C. for 8 hours in a stream of nitrogen. After a reaction product was allowed to cool to room temperature, methanol was added to the reaction product and a generated precipitate was filtrated off. The precipitate was subjected to purification by silica gel column chromatography using chloroform as a eluent to yield 480 mg (42% yield) of Exemplary Compound XG-1.

$^1$H NMR (CDCl$_3$, 500 MHz) σ(ppm): 7.96 (m, 3H), 7.77 (m, 3H), 7.35 (m, 6H), 7.22 (m, 3H), 6.85 (m, 6H), 6.77 (m, 3H), 3.70 (m, 3H), 3.48 (m, 3H), 2.68 (m, 3H), 2.47 (m, 3H).

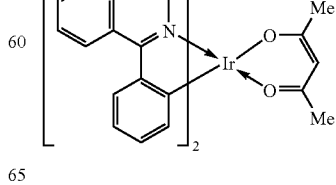

XC-1

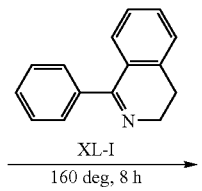

General Formula (39)

XL-I

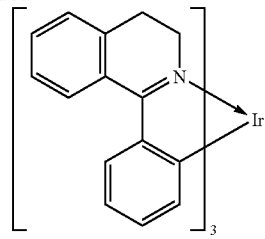

XG 1

Example 4

In this example, a device having 3 organic layers as shown in FIG. 2 was used as a device constitution.

ITO (transparent electrode 14) having a thickness of 100 nm was patterned onto a glass substrate (transparent substrate 15) to have an opposite electrode area of 3 mm². The following organic layers and electrode layers were successively formed on the ITO substrate through vacuum evaporation according to resistance heating in a vacuum chamber at 10-4 Pa to produce a device.

Organic layer 1 (hole-transporting layer 13) (40 nm): α-NPD
Organic layer 2 (light-emitting layer 12) (30 nm): CBP:XC-1 (weight ratio of 5% by weight)
Organic layer 3 (electron-transporting layer 16) (30 nm): Alq₃
Metal electrode layer 1 (15 nm): Al/Li alloy (Li content of 1.8% by weight)
Metal electrode layer 2 (100 nm): Al Electric field was applied to the device in such a manner that the ITO side served as an anode and the Al side served as a cathode. As a result, stable red luminance was observed.

Example 5

A device was prepared in the same manner as in Example 4 except that Exemplary Compound XG-1 was used instead of Exemplary Compound XC-1. Electric field was applied to the device in such a manner that the ITO side served as an anode and the Al side served as a cathode. As a result, stable red luminance was observed.

Example 6

(Synthesis of Exemplary Compound XA-6)

Exemplary Compound XA-6 can be synthesized in the same manner as in Examples 1 and 2 except that Compound XL-2 is used instead of Compound XL-1 used in Example 1.

General Formula (40)

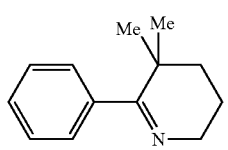

XL-2

Example 7

(Synthesis of Exemplary Compound XE-6)

Exemplary Compound XE-6 can be synthesized in the same manner as in Example 3 except that Exemplary Compound XA-6 and Compound XL-2 are used instead of Exemplary Compound XC-1 and Compound XL-1 used in Example 3, respectively.

Example 8

(Synthesis of Exemplary Compound XA-12)

Exemplary Compound XA-12 can be synthesized in the same manner as in Examples 1 and 2 except that Compound XL-3 is used instead of Compound XL-1 used in Example 1.

General Formula (41)

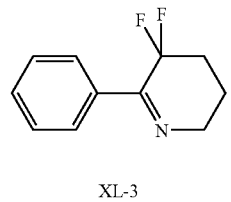

XL-3

Example 9

(Synthesis of Exemplary Compound XE-12)

Exemplary Compound XE-12 can be synthesized in the same manner as in Example 3 except that Exemplary Compound XA-12 and Compound XL-3 are used instead of Exemplary Compound XC-1 and Compound XL-1 used in Example 3, respectively.

Example 10

(Synthesis of Exemplary Compound XA-20)

Exemplary Compound XA-20 can be synthesized in the same manner as in Examples 1 and 2 except that Compound XL-4 was used instead of Compound XL-1 used in Example 1.

General Formula (42)

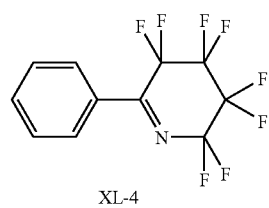

XL-4

Example 11

(Synthesis of Exemplary Compound XE-20)

Exemplary Compound XE-20 can be synthesized in the same manner as in Example 3 except that Exemplary Compound XA-20 and Compound XL-4 are used instead of Exemplary Compound XC-1 and Compound XL-1 used in Example 3, respectively.

Example 12

(Synthesis of Exemplary Compound XA-23)

Exemplary Compound XA-23 can be synthesized in the same manner as in Examples 1 and 2 except that Compound XL-5 was used instead of Compound XL-1 used in Example 1.

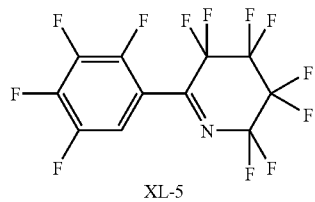

General Formula (43)

XL-5

Example 13

(Synthesis of Exemplary Compound XE-23)

Exemplary Compound XE-23 can be synthesized in the same manner as in Example 3 except that Exemplary Compound XA-23 and Compound XL-5 are used instead of Exemplary Compound XC-1 and Compound XL-1 used in Example 3, respectively.

Example 14

(Synthesis of Exemplary Compound XA-25)

Exemplary Compound XA-25 can be synthesized in the same manner as in Examples 1 and 2 except that Compound XL-6 is used instead of Compound XL-1 used in Example 1.

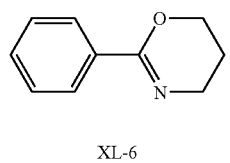

General Formula (44)

XL-6

Example 15

(Synthesis of Exemplary Compound XE-28)

Exemplary Compound XE-28 can be synthesized in the same manner as in Example 3 except that Exemplary Compound XA-25 and Compound XL-6 are used instead of Exemplary Compound XC-1 and Compound XL-1 used in Example 3, respectively.

Example 16

(Synthesis of Exemplary Compound XA-35)

Exemplary Compound XA-35 can be synthesized in the same manner as in Examples 1 and 2 except that Compound XL-7 is used instead of Compound XL-1 used in Example 1.

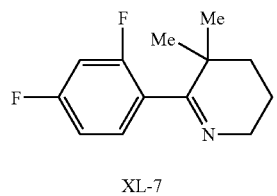

General Formula (45)

XL-7

Example 17

(Synthesis of Exemplary Compound XE-35)

Exemplary Compound XE-35 can be synthesized in the same manner as in Example 3 except that Exemplary Compound XA-35 and Compound XL-7 are used instead of Exemplary Compound XC-1 and Compound XL-1 used in Example 3, respectively.

Example 18

(Synthesis of Exemplary Compound XA-37)

Exemplary Compound XA-37 can be synthesized in the same manner as in Examples 1 and 2 except that Compound XL-8 is used instead of Compound XL-1 used in Example 1.

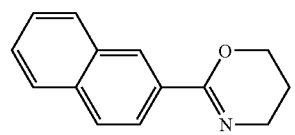

General Formula (46)

XL-8

Example 19

(Synthesis of Exemplary Compound XE-37)

Exemplary Compound XE-37 can be synthesized in the same manner as in Example 3 except that Exemplary Compound XA-37 and Compound XL-8 are used instead of Exemplary Compound XC-1 and Compound XL-1 used in Example 3, respectively.

Example 20

(Synthesis of Exemplary Compound XA-42)

Exemplary Compound XA-42 can be synthesized in the same manner as in Examples 1 and 2 except that Compound XL-9 is used instead of Compound XL-1 used in Example 1.

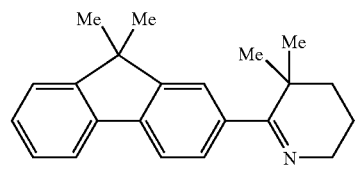

General Formula (47)

XL 9

Example 21

(Synthesis of Exemplary Compound XE-42)

Exemplary Compound XE-42 can be synthesized in the same manner as in Example 3 except that Exemplary Compound XA-42 and Compound XL-9 are used instead of Exemplary Compound XC-1 and Compound XL-1 which were used in Example 3, respectively.

Example 22

(Synthesis of Exemplary Compound XA-55)

Exemplary Compound XA-55 can be synthesized in the same manner as in Examples 1 and 2 except that Compound XL-10 is used instead of Compound XL-1 used in Example 1.

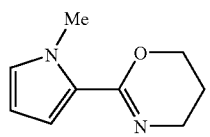

General Formula (48)

XL-10

Example 23

(Synthesis of Exemplary Compound XE-55)

Exemplary Compound XE-55 can be synthesized in the same manner as in Example 3 except that Exemplary Compound XA-55 and Compound XL-10 are used instead of Exemplary Compound XC-1 and Compound XL-1 used in Example 3, respectively.

Example 24

(Synthesis of Exemplary Compound XB-3)

Exemplary Compound XB-3 can be synthesized in the same manner as in Examples 1 and 2 except that Compound XL-11 is used instead of Compound XL-1 used in Example 1.

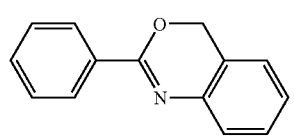

General Formula (49)

XL 11

Example 25

(Synthesis of Exemplary Compound XF-3)

Exemplary Compound XF-3 can be synthesized in the same manner as in Example 3 except that Exemplary Compound XB-3 and Compound XL-11 are used instead of Exemplary Compound XC-1 and Compound XL-1 used in Example 3, respectively.

Example 26

(Synthesis of Exemplary Compound XC-3)

Exemplary Compound XC-3 can be synthesized in the same manner as in Examples 1 and 2 except that Compound XL-12 is used instead of Compound XL-1 used in Example 1.

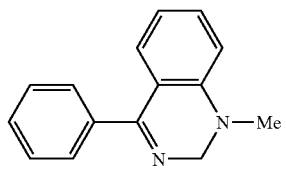

General Formula (50)

XL-12

Example 27

(Synthesis of Exemplary Compound XG-3)

Exemplary Compound XG-3 can be synthesized in the same manner as in Example 3 except that Exemplary Compound XC-3 and Compound XL-12 are used instead of Exemplary Compound XC-1 and Compound XL-1 used in Example 3, respectively.

Example 28

(Synthesis of Exemplary Compound XC-6)

Exemplary Compound XC-6 can be synthesized in the same manner as in Examples 1 and 2 except that Compound XL-13 is used instead of Compound XL-1 used in Example 1.

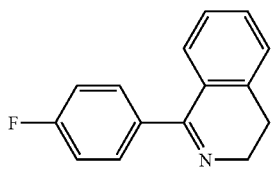

General Formula (51)

XL-13

Example 29

(Synthesis of Exemplary Compound XG-9)

Exemplary Compound XG-9 can able to be synthesized in the same manner as in Example 3 except that Exemplary Compound XC-3 and Compound XL-13 are used instead of Exemplary Compound XC-1 and Compound XL-1 used in Example 3, respectively.

Example 30

(Synthesis of Exemplary Compound XC-8)

Exemplary Compound XC-8 can be synthesized in the same manner as in Examples 1 and 2 except that Compound XL-14 is used instead of Compound XL-1 used in Example 1.

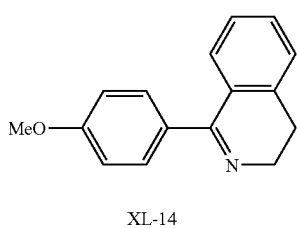

XL-14

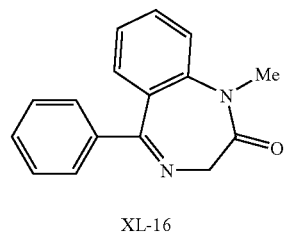

XL-16

Example 31

(Synthesis of Exemplary Compound XG-5)

Exemplary Compound XG-5 can be synthesized in the same manner as in Example 3 except that Exemplary Compound XC-8 and Compound XL-14 are used instead of Exemplary Compound XC-1 and Compound XL-1 used in Example 3, respectively.

Example 32

(Synthesis of Exemplary Compound XC-10)

Exemplary Compound XC-10 can be synthesized in the same manner as in Examples 1 and 2 except that Compound XL-15 is used instead of Compound XL-1 used in Example 1.

Example 35

(Synthesis of Exemplary Compound XG-13)

Exemplary Compound XG-13 can be synthesized in the same manner as in Example 3 except that Exemplary Compound XC-13 and Compound XL-16 are used instead of Exemplary Compound XC-1 and Compound XL-1 used in Example 3, respectively.

Example 36

(Synthesis of Exemplary Compound XD-1)

Exemplary Compound XD-1 can be synthesized in the same manner as in Examples 1 and 2 except that Compound XL-17 is used instead of Compound XL-1 used in Example 1.

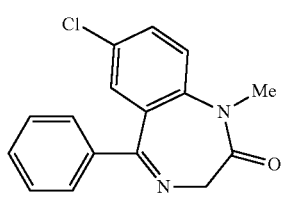

XL 15

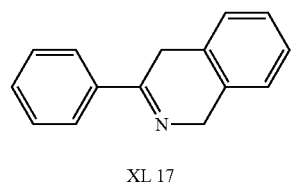

XL 17

Example 33

(Synthesis of Exemplary Compound XG-10)

Exemplary Compound XG-10 can be synthesized in the same manner as in Example 3 except that Exemplary Compound XC-10 and Compound XL-15 are used instead of Exemplary Compound XC-1 and Compound XL-1 used in Example 3, respectively.

Example 34

(Synthesis of Exemplary Compound XC-13)

Exemplary Compound XC-13 can be synthesized in the same manner as in Examples 1 and 2 except that Compound XL-16 is used instead of Compound XL-1 used in Example 1.

Example 37

(Synthesis of Exemplary Compound XH-1)

Exemplary Compound XH-1 can be synthesized in the same manner as in Example 3 except that Exemplary Compound XD-1 and Compound XL-17 are used instead of Exemplary Compound XC-1 and Compound XL-1 used in Example 3, respectively.

Example 38

(Synthesis of Exemplary Compound XD-2)

Exemplary Compound XD-2 can be synthesized in the same manner as in Examples 1 and 2 except that Compound XL-18 is used instead of Compound XL-1 used in Example 1.

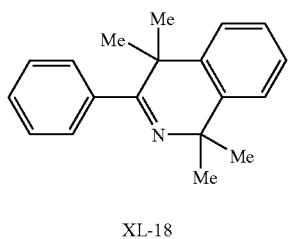

XL-18

Example 39

(Synthesis of Exemplary Compound XH-2)

Exemplary Compound XH-2 can be synthesized in the same manner as in Example 3 except that Exemplary Compound XD-2 and Compound XL-18 are used instead of Exemplary Compound XC-1 and Compound XL-1 used in Example 3, respectively.

Example 40

(Synthesis of Exemplary Compound XD-6)

Exemplary Compound XD-6 can be synthesized in the same manner as in Examples 1 and 2 except that Compound XL-19 is used instead of Compound XL-1 used in Example 1.

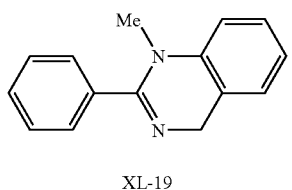

XL-19

Example 41

(Synthesis of Exemplary Compound XH-6)

Exemplary Compound XH-6 can be synthesized in the same manner as in Example 3 except that Exemplary Compound XD-6 and Compound XL-19 are used instead of Exemplary Compound XC-1 and Compound XL-1 used in Example 3, respectively.

Example 42

(Synthesis of Exemplary Compound XD-7)

Exemplary Compound XD-7 can be synthesized in the same manner as in Examples 1 and 2 except that Compound XL-20 is used instead of Compound XL-1 used in Example 1.

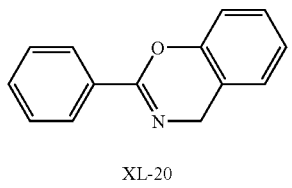

XL-20

Example 43

(Synthesis of Exemplary Compound XH-7)

Exemplary Compound XH-7 can be synthesized in the same manner as in Example 3 except that Exemplary Compound XD-7 and Compound XL-20 are used instead of Exemplary Compound XC-1 and Compound XL-1 used in Example 3, respectively.

INDUSTRIAL APPLICABILITY

The metal complex of the present invention having a structure in which a nitrogen atom in a 6- to 8-membered non-aromatic cyclic group is bonded to a metal atom can be utilized for a light-emitting device excellent in emitting light with high efficiency. In addition, the light-emitting device of the present invention can provide phosphorescent luminescence of a red color when the light-emitting device is used as a display device, hence the light-emitting device of the present invention can be utilized for a display apparatus such as a full-color apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application. 2006-099894, filed Mar. 31, 2006 which is hereby incorporated by reference herein in its entirety.

What is claimed is:

1. A metal complex represented by any one of the following formulas:

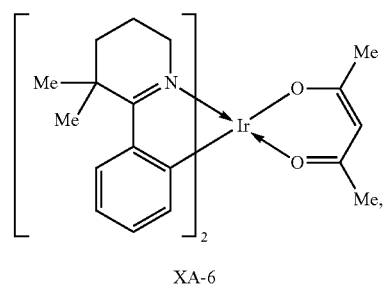

XA-6

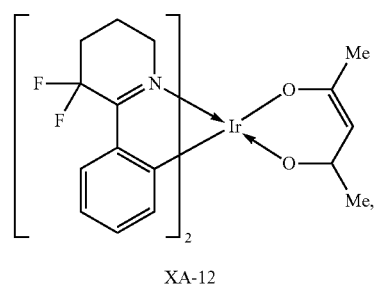

XA-12

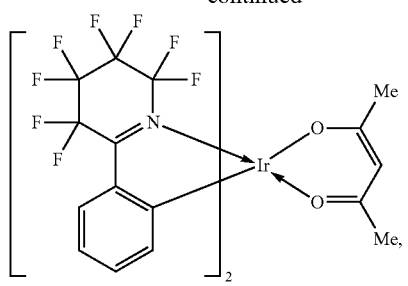
XA-20
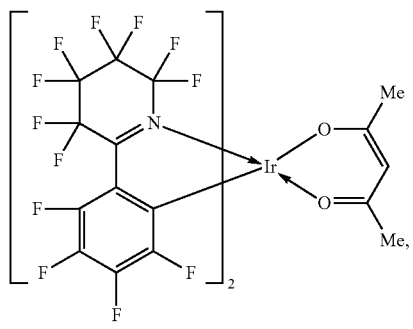
XA-23
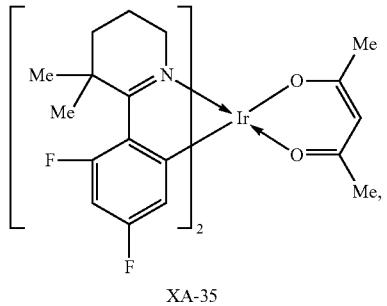
XA-35
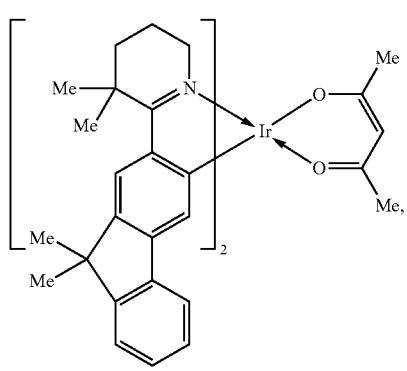
XA-42
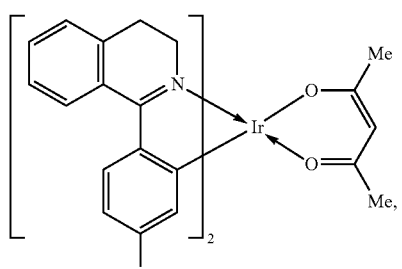
XC-6
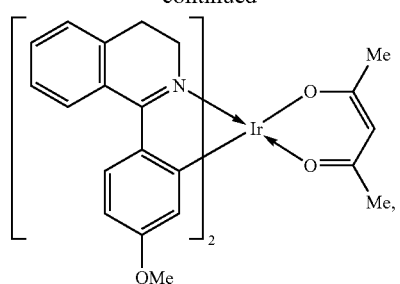
XC-8
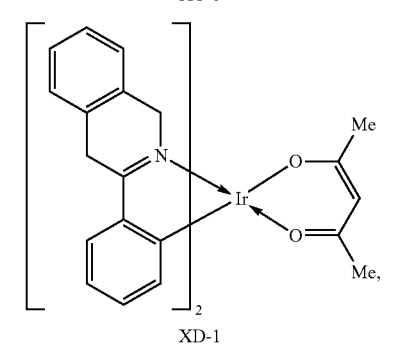
XD-1
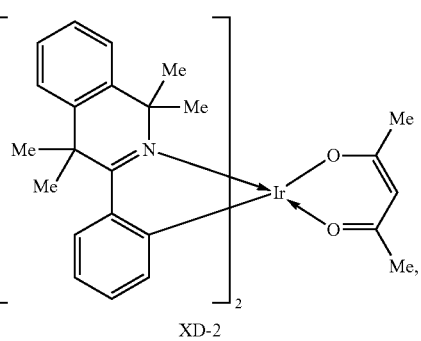
XD-2
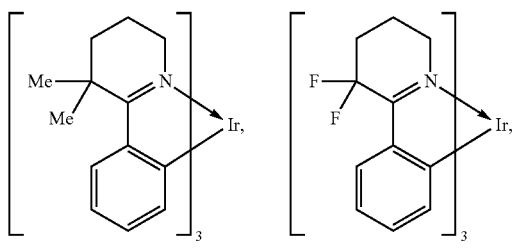
XE-6
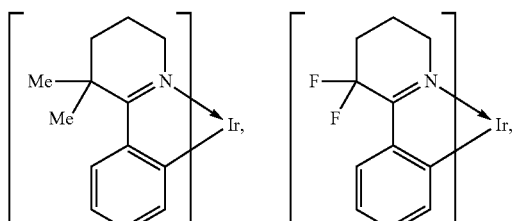
XE-12
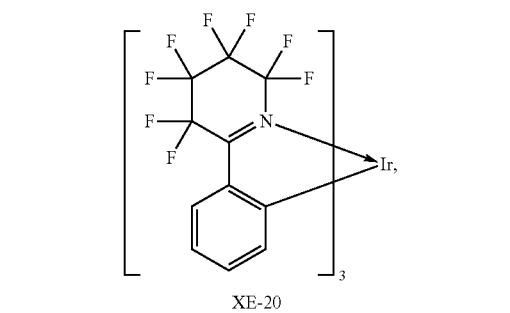
XE-20

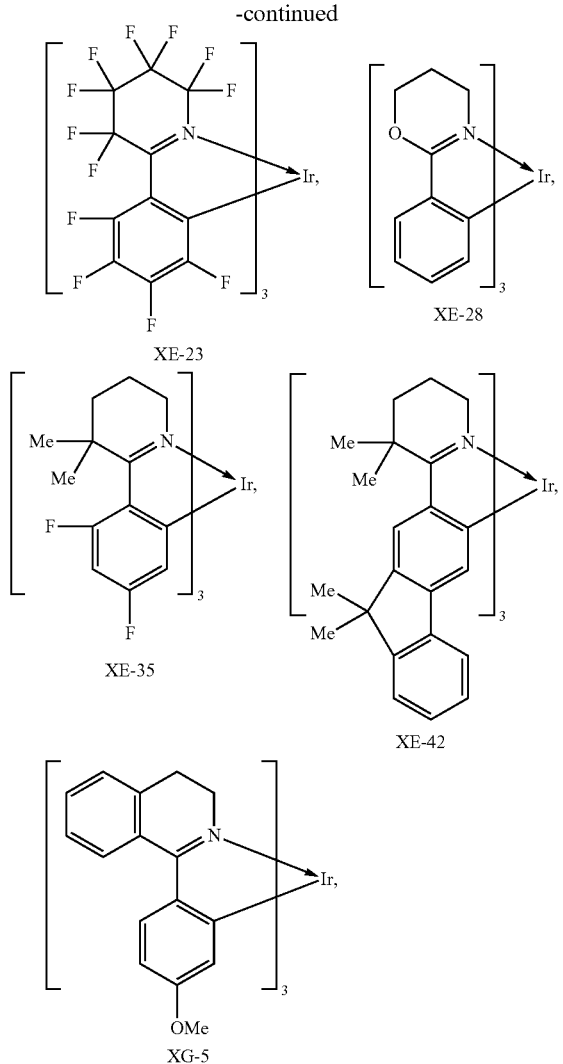
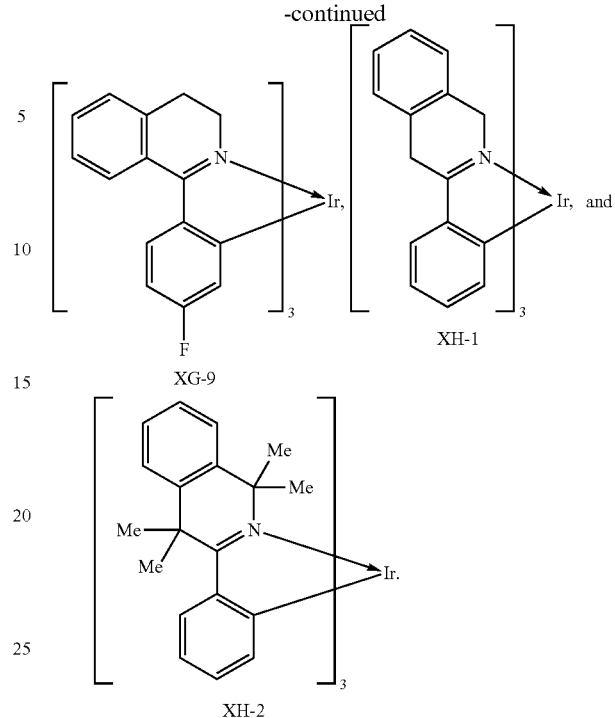

2. An organic light-emitting device comprising:
   a pair of electrodes; and
   an organic compound layer interposed between the electrodes,
   wherein the organic compound layer includes the metal complex according to claim 1.

3. An organic light-emitting device according to claim 2, wherein the organic compound layer is a light-emitting layer.

4. A display apparatus comprising the organic light-emitting device according to claim 3.

* * * * *